US009504699B2

(12) United States Patent
Schaeffler

(10) Patent No.: US 9,504,699 B2
(45) Date of Patent: *Nov. 29, 2016

(54) DELAYED-RELEASE GLUCOCORTICOID TREATMENT OF RHEUMATOID DISEASE

(71) Applicant: Horizon Pharma AG, Reinach (CH)

(72) Inventor: Achim Schaeffler, Beerfelden (DE)

(73) Assignee: HZNP Limited, Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 14/563,000

(22) Filed: Dec. 8, 2014

(65) Prior Publication Data

US 2015/0141388 A1    May 21, 2015

Related U.S. Application Data

(63) Continuation of application No. 13/860,015, filed on Apr. 10, 2013, now Pat. No. 8,920,838, which is a continuation of application No. 13/176,598, filed on Jul. 5, 2011, now abandoned, which is a continuation of application No. 11/833,322, filed on Aug. 3, 2007, now abandoned.

(60) Provisional application No. 60/835,093, filed on Aug. 3, 2006.

(51) Int. Cl.
| | |
|---|---|
| A61K 9/22 | (2006.01) |
| A61K 9/48 | (2006.01) |
| A61P 19/02 | (2006.01) |
| C07J 5/00 | (2006.01) |
| A61K 31/573 | (2006.01) |
| A61K 9/28 | (2006.01) |
| A61K 45/06 | (2006.01) |

(52) U.S. Cl.
CPC ............... *A61K 31/573* (2013.01); *A61K 9/28* (2013.01); *A61K 45/06* (2013.01)

(58) Field of Classification Search
None
See application file for complete search history.

(56) References Cited

U.S. PATENT DOCUMENTS

| | | |
|---|---|---|
| 3,048,526 A | 8/1962 | Boswell |
| 3,125,491 A | 3/1964 | Elowe et al. |
| 3,146,169 A | 8/1964 | Stephenson et al. |
| 3,870,790 A | 3/1975 | Lowey et al. |
| 4,012,497 A | 3/1977 | Schopftin |
| 4,797,288 A | 1/1989 | Shanna et al. |
| 4,865,849 A | 9/1989 | Conte et al. |
| 4,867,985 A | 9/1989 | Heafield et al. |
| 4,871,549 A | 10/1989 | Ueda et al. |

(Continued)

FOREIGN PATENT DOCUMENTS

| | | |
|---|---|---|
| DE | 1020040 43 863 A1 | 3/2006 |
| EP | 0 274 734 | 6/1991 |

(Continued)

OTHER PUBLICATIONS

Gotlieb (Treatment of Rheumatoid Arthritis and Osteoarthritis: A Guide to the General Practitioner/Family Physician; Jan. 2005); Wayback dated to Jul. 29, 2005; downloaded Feb. 26, 2015.*

(Continued)

*Primary Examiner* — Jeffrey T Palenik

(57) ABSTRACT

The present invention refers to the treatment of a rheumatic disease and/or osteoarthritis by administering a delayed-release dosage form of a glucocorticoid to a subject in need thereof.

9 Claims, 3 Drawing Sheets

(56) References Cited

U.S. PATENT DOCUMENTS

| | | |
|---|---|---|
| 4,966,770 A | 10/1990 | Giannini et al. |
| 5,004,614 A | 4/1991 | Staniforth |
| 5,171,580 A | 12/1992 | Iamartino et al. |
| 5,279,832 A | 1/1994 | Greissinger et al. |
| 5,310,558 A | 5/1994 | Pozzi et al. |
| 5,310,578 A | 5/1994 | Thum-Millier et al. |
| 5,316,772 A | 5/1994 | Jurgens, Jr. et al. |
| 5,425,950 A | 6/1995 | Dandiker et al. |
| 5,456,920 A | 10/1995 | Matoba et al. |
| 5,464,633 A | 11/1995 | Conte et al. |
| 5,468,221 A | 11/1995 | Schoner |
| 5,519,057 A | 5/1996 | Loew et al. |
| 5,567,696 A | 10/1996 | McGuire et al. |
| 5,698,221 A | 12/1997 | Patel et al. |
| 5,702,723 A | 12/1997 | Griffin |
| 5,709,880 A | 1/1998 | Del Corral et al. |
| 5,716,648 A | 2/1998 | Halskov et al. |
| 5,788,987 A | 8/1998 | Busetti et al. |
| 5,792,476 A | 8/1998 | Hallgren |
| 5,840,332 A | 11/1998 | Lerner et al. |
| 5,900,252 A | 5/1999 | Calanchi et al. |
| 6,013,280 A | 1/2000 | Frisbee |
| 6,020,356 A | 2/2000 | Guglielmotti et al. |
| 6,183,780 B1 | 2/2001 | Van Balken et al. |
| 6,190,591 B1 | 2/2001 | Van Lengerich |
| 6,210,710 B1 | 4/2001 | Skinner |
| 6,217,903 B1 | 4/2001 | Skinner |
| 6,245,352 B1 | 6/2001 | Arbuthnot |
| 6,248,363 B1 | 6/2001 | Patel et al. |
| 6,267,985 B1 | 7/2001 | Chen et al. |
| 6,294,192 B1 | 9/2001 | Patel et al. |
| 6,294,200 B1 | 9/2001 | Conte et al. |
| 6,309,663 B1 | 10/2001 | Patel et al. |
| 6,358,525 B1 | 3/2002 | Guo et al. |
| 6,365,185 B1 | 4/2002 | Ritschel et al. |
| 6,375,986 B1 | 4/2002 | Ryde et al. |
| 6,428,809 B1 | 8/2002 | Abrams et al. |
| 6,488,960 B1 | 12/2002 | Bardsley |
| 6,500,459 B1 | 12/2002 | Chhabra et al. |
| 6,565,873 B1 | 5/2003 | Shefer et al. |
| 6,589,562 B1 | 7/2003 | Shefer et al. |
| 6,599,284 B2 | 7/2003 | Faour |
| 6,602,521 B1 | 8/2003 | Ting et al. |
| 6,620,439 B1 | 9/2003 | Mehta |
| 6,635,279 B2 | 10/2003 | Kolter et al. |
| 6,677,326 B2 | 1/2004 | Bardsley et al. |
| 6,733,784 B1 | 5/2004 | Ayres |
| 6,761,903 B2 | 7/2004 | Chen et al. |
| 6,887,493 B2 | 5/2005 | Shafer et al. |
| 6,908,626 B2 | 6/2005 | Cooper et al. |
| 7,074,426 B2 | 7/2006 | Kochinke |
| RE39,239 E | 8/2006 | Busetti et al. |
| 7,163,700 B2 | 1/2007 | Bogue |
| 7,201,923 B1 | 4/2007 | Van Lengerich |
| 7,241,805 B2 | 7/2007 | Oberegger et al. |
| 7,384,653 B2 | 6/2008 | Wright et al. |
| 7,413,750 B2 | 8/2008 | Kolter et al. |
| 7,704,527 B2 | 4/2010 | Hirsh et al. |
| 7,776,345 B2 | 8/2010 | Dudhara et al. |
| 8,168,218 B2 | 5/2012 | Vergnault et al. |
| 8,309,124 B2 | 11/2012 | Vergnault |
| 8,394,407 B2 | 3/2013 | Vergnault |
| 8,920,838 B2 | 12/2014 | Schaeffler |
| 2001/0024658 A1 | 9/2001 | Chen et al. |
| 2001/0038852 A1 | 11/2001 | Kolter et al. |
| 2002/0012680 A1 | 1/2002 | Patel et al. |
| 2002/0045646 A1 | 4/2002 | Phillips |
| 2003/0021841 A1 | 1/2003 | Matharu et al. |
| 2003/0035836 A1 | 2/2003 | Shanghvi et al. |
| 2003/0044458 A1 | 3/2003 | Wright et al. |
| 2003/0055028 A1 | 3/2003 | Stergiopoulos et al. |
| 2003/0064097 A1 | 4/2003 | Patel et al. |
| 2003/0203030 A1 | 10/2003 | Ashton et al. |
| 2003/0215513 A1 | 11/2003 | Fyhr et al. |
| 2004/0018327 A1 | 1/2004 | Wynn et al. |
| 2004/0033267 A1 | 2/2004 | Merisko-Liversidge et al. |
| 2004/0062778 A1 | 4/2004 | Shefer et al. |
| 2004/0121010 A1 | 6/2004 | Hirsh et al. |
| 2004/0156895 A1 | 8/2004 | Pruitt et al. |
| 2004/0185097 A1 | 9/2004 | Kannan et al. |
| 2004/0234602 A1 | 11/2004 | Fischer et al. |
| 2004/0253310 A1 | 12/2004 | Fischer et al. |
| 2005/0008702 A1 | 1/2005 | Faour et al. |
| 2006/0057200 A1 | 3/2006 | Schaeffler |
| 2006/0153916 A1 | 7/2006 | Vaya et al. |
| 2006/0177507 A1 | 8/2006 | Faour et al. |
| 2006/0210631 A1 | 9/2006 | Patel et al. |
| 2007/0110807 A1 | 5/2007 | Vergnault et al. |
| 2007/0111978 A1 | 5/2007 | Dohil et al. |
| 2007/0148229 A1 | 6/2007 | Vergnault et al. |
| 2008/0014272 A1 | 1/2008 | Skolnick et al. |
| 2008/0026040 A1 | 1/2008 | Farr et al. |
| 2008/0038346 A1 | 2/2008 | Eisenreich et al. |
| 2008/0057086 A1 | 3/2008 | Etter |
| 2008/0057123 A1 | 3/2008 | Grenier et al. |
| 2008/0076743 A1 | 3/2008 | Schaeffler |
| 2008/0113002 A1 | 5/2008 | Yedgar et al. |
| 2008/0145438 A1 | 6/2008 | Bogue |
| 2008/0166303 A1 | 7/2008 | Tamarkin et al. |
| 2008/0181932 A1 | 7/2008 | Bortz et al. |
| 2008/0213374 A1 | 9/2008 | Carty et al. |
| 2008/0220074 A1 | 9/2008 | Bosch et al. |
| 2008/0248107 A1 | 10/2008 | Pilgaonkar et al. |
| 2008/0286343 A1 | 11/2008 | Cengic et al. |
| 2008/0311162 A1 | 12/2008 | Darmuzey et al. |
| 2008/0317841 A1 | 12/2008 | Grenier et al. |
| 2009/0053310 A1 | 2/2009 | Pilgaonkar et al. |
| 2009/0068236 A1 | 3/2009 | Brown et al. |
| 2009/0098200 A1 | 4/2009 | Temtsin et al. |
| 2009/0123390 A1 | 5/2009 | Hill |
| 2009/0220611 A1 | 9/2009 | Dargelas et al. |
| 2009/0297533 A1 | 12/2009 | Lichter et al. |
| 2009/0324710 A1 | 12/2009 | Glidden et al. |
| 2009/0325860 A1 | 12/2009 | Costantino et al. |
| 2010/0016322 A1 | 1/2010 | Nagaraju et al. |
| 2010/0105717 A1 | 4/2010 | Gordon et al. |
| 2010/0113416 A1 | 5/2010 | Friedman et al. |
| 2010/0136125 A1 | 6/2010 | Jacobus et al. |
| 2010/0151038 A1 | 6/2010 | Cabelka et al. |
| 2010/0189770 A1 | 7/2010 | Crutchley et al. |
| 2010/0196427 A1 | 8/2010 | Schaffler |
| 2010/0222312 A1 | 9/2010 | Witte et al. |
| 2012/0070499 A1 | 3/2012 | Schaeffler et al. |
| 2012/0177739 A1 | 7/2012 | Vergnault et al. |
| 2012/0213910 A1 | 8/2012 | Schaeffler et al. |
| 2013/0122061 A1 | 5/2013 | Vergnault |
| 2013/0190279 A1 | 7/2013 | Schaeffler et al. |
| 2014/0328912 A1 | 11/2014 | Vergnault |
| 2014/0348918 A1 | 11/2014 | Witte |
| 2014/0349980 A1 | 11/2014 | Schäffler |

FOREIGN PATENT DOCUMENTS

| | | |
|---|---|---|
| EP | 0 463 877 | 1/1992 |
| EP | 0 519 099 | 12/1992 |
| EP | 0 638 310 | 2/1995 |
| EP | 0 673 645 | 9/1995 |
| EP | 0 776 660 | 6/1997 |
| EP | 1 027 888 | 8/2000 |
| EP | 0 939 623 | 2/2002 |
| EP | 1 275 381 | 1/2003 |
| EP | 1 067 910 | 5/2004 |
| EP | 1 411 901 B1 | 8/2010 |
| FR | 1603314 A | 4/1971 |
| GB | 0 860 708 | 2/1961 |
| GB | 0 874 586 | 8/1961 |
| GB | 1346609 | 2/1974 |
| JP | 2001-010950 | 1/2001 |
| JP | 2002-539167 A | 11/2002 |
| WO | WO-92/00064 A1 | 1/1992 |
| WO | WO-92/11845 A1 | 7/1992 |
| WO | WO-93/19741 A1 | 10/1993 |
| WO | WO-94/07470 | 4/1994 |
| WO | WO-95/08323 | 3/1995 |

(56) References Cited

FOREIGN PATENT DOCUMENTS

| | | |
|---|---|---|
| WO | WO-96/40078 A1 | 12/1996 |
| WO | WO-97/27843 A2 | 8/1997 |
| WO | WO-98/13029 | 4/1998 |
| WO | WO-99/01121 | 1/1999 |
| WO | WO-99/18938 | 4/1999 |
| WO | WO-99/51208 | 10/1999 |
| WO | WO-00/18447 | 4/2000 |
| WO | WO-00/54780 A2 | 9/2000 |
| WO | WO-01/08421 | 2/2001 |
| WO | WO-01/52819 | 7/2001 |
| WO | WO-01/68056 A1 | 9/2001 |
| WO | WO-01/80824 | 11/2001 |
| WO | WO-02/00204 A1 | 1/2002 |
| WO | WO-02/072033 A2 | 9/2002 |
| WO | WO-02/072034 A2 | 9/2002 |
| WO | WO-03/011255 | 2/2003 |
| WO | WO-03/075919 A1 | 9/2003 |
| WO | WO-03/026626 A2 | 10/2003 |
| WO | WO-2004/103349 A2 | 2/2004 |
| WO | WO-2004/028510 A1 | 4/2004 |
| WO | WO-2004/093843 A1 | 11/2004 |
| WO | WO-2004/093850 A1 | 11/2004 |
| WO | WO-2005/025542 A1 | 3/2005 |
| WO | WO-2005/027843 A2 | 3/2005 |
| WO | WO-2006/010394 A2 | 2/2006 |
| WO | WO-2006/027266 A1 | 3/2006 |
| WO | WO-2006/099445 A2 | 9/2006 |
| WO | WO-2007/064912 A2 | 6/2007 |
| WO | WO-2008/015018 A1 | 2/2008 |
| WO | WO-2008/033351 | 3/2008 |
| WO | WO-2008/079963 | 7/2008 |
| WO | WO-2008/081175 | 7/2008 |
| WO | WO-2008/134071 | 11/2008 |
| WO | WO-2008/140459 | 11/2008 |
| WO | WO-2008/140460 | 11/2008 |
| WO | WO-2008/148798 | 12/2008 |
| WO | WO-2009/022355 | 2/2009 |
| WO | WO-2009/042778 | 4/2009 |
| WO | WO-2009/047799 | 4/2009 |
| WO | WO-2009/047802 | 4/2009 |
| WO | WO-2009/085271 | 7/2009 |
| WO | WO-2009/085274 | 7/2009 |
| WO | WO-2009/085275 | 7/2009 |
| WO | WO-2009110005 | 9/2009 |
| WO | WO-2009/142772 | 11/2009 |
| WO | WO-2009/152479 | 12/2009 |
| WO | WO-2010/005687 | 1/2010 |

OTHER PUBLICATIONS

NPL search history; downloaded Feb. 26, 2015; pdf, 2 pages.*
Sterapred product specification, Nov. 2003.
Sokka, "Assessment of pain in rheumatic diseases," Clin. Exp. Rheumatol. 2005; (Suppl. 39):S77-S84.
Townsend et al., Glucocorticoid use in rheumatoid arthritis: Benefits, mechanisms, and risks, Clinical and experimental rheumatology, 2004, vol. 22, pp. S77-S82.
Hudson et al., "Morning Stiffness Is a Better Predictor of Function in early Inflammatory Arthritis than Are Swollen and Tender Joints," Arthritis Rheum 2005;52 Suppl 9: abstract 1036.
U.S. Appl. No. 14/305,165, Office Action dated Jan. 28, 2015.
Second Amended Invalidity Contentions, Horizon Pharma AG et al. -v- Watson Laboratories, Inc.—Florida, et al., U.S. District Court for the District of New Jersey, (Civil Action No. 13-5124 (JEI/JS)) Dec. 30, 2014.
Second Amended Invalidity Contentions Narrative, Horizon Pharma AG et al. -v- Watson Laboratories, Inc.—Florida, et al., U.S. District Court for the District of New Jersey, (Civil Action No. 13-5124 (JEI/JS)) Dec. 30, 2014.
U.S. Appl. No. 12/484,493, filed Jun. 15, 2009, Kirwan et al.
Guidelines for the Management of Rheumatoid Arthritis, 2002 Update, American College of. Rheumatology Subcommittee on Rheumatoid Arthritis Guidelines, Arthritis & Rheumatism (2):328-346, Feb. 2002.

Ahlmen et al., Rheumatology Outcomes: the Patients Perspective, a Multicentre Focus Group Interview Study of Swedish Rheumatoid Arthritis Patents, Rheumatism 44: 105-110, 2005.
Arnett et al., The American rheumatism association 1987 revised criteria for the classification of rheumatoid arthritis, Arthritis & Rheumatism, vol. 31, Issue 3, pp. 315-324, Mar. 1988.
Arvidson et al., Circadian rhythm of serum interleukin-6 in rheumatoid arthritis, Ann Rheum Dis1994;53:521-524.
Arvidson et al., The timing of glucocorticoid administration in rheumatoid arthritis, Ann Rheum Dis1997;56:27-31.
Aulton, M. "Pharmaceutics: The Science of Dosage Form Design" Churchill Livingstone (1988), pp. 307-309.
AXELROD Glucocorticoid Therapy, Medicine 55:1, 1976, 39-65.
Biljsma et al., Developments of Glucocorticoid Therapy, Rheumatoid Disease Clinics of North America, 31:1-17, 2005.
Biljsma et al., Glucocorticoids in-the Treatment of Early and late RA. Annals of the Rheumatic Diseases 62(11): 1033-1037 Nov. 2003.
Bloom, "Betamethasone" British Journal of Medicine, Sep. 16, 1961, 767.
Boers et al., "Glucocorticoids in Rheumatoid Arthritis: a Senescent Research Agenda on the Brink of Rejuvenation?" Best Practice & Research Clinical Rheumatology 18(1):21-29. 2004.
Buttgereit et al., "The Molecular basis for the Effectiveness, Toxicity, and Resistance to Glucocorticoids: Focus on the Treatment of Rheumatoid Arthritis," Scand J. Rheumatol 34: 14-21, 2005.
Buttgereit et al., "New Modified-release (MR) Tablet Formulation of Prednisone Significantly Reduces Duration of Morning Stiffness Compared to Standard Prednisone in Subjects With Rheumatoid Arthritis (RA)," Arthritis and Rheumatism, Dec. 2006, vol. 54, No. 12, pp. 4036-4038.
Buttgereit et al. Efficacy of Modified-Release Versus Standard Prednisone to Reduce Duration of Morning Stiffness of the Joints in Rheumatoid Arthritis (CAPRA1):A Double-Bind, Randomized Controlled Trial Lancet 371, 2008, 205-14.
Buttgereit et al., "Glucocorticoids in the Treatment of Rheumatic Diseases," Arthritis & Rheumatism. 50(111:3408-3417 Nov. 2004.
Buttgereit et al., Optimized Glucocorticoid Therapy: the Sharpening of an Old Spear, The Lancet 365:801-803, Feb. 26, 2005.
Buttgereit et al., "Targeting Pathophysiological Rhythms: Prednisone chronotherapy Shows Sustained Efficacy in Rheumatoid Arthritis." Ann Rheum Dis; 2010; 7 pages.
Capell et al., "Lack of Radiological and Clinical Benefit Over Two Years of flow Dose Prednisolone for Rheumatoid Arthritis: Results of a Randomized Controlled Trial," Ann. Rheum Dis 63: 797-803, 2004.
Carr et al., "Rheumatology Outcomes: the Patient's Perspective." Journal of Rheumatology 30(4): 880-883, 2003.
Conn, Resolved: Low-Dose Prednisone is Indicated as a Standard Treatment in Patients with Rheumatoid Arthritis: Arthritis Care & Research 45:462-467, 2001.
Conte et al, "Press-Coated Tablets for Time Programmed Release of Drugs." Biomat. 14-13(1993):1017-1023.
CPMP/EWP/556195; published Dec. 17, 2003.
Crofford et al., circadian Relationships Between Interleukin {IL*6}and Hypothalamic-pituitary—adrenal Axis Hormones• Failure of 11-6 to Cause Sustained Hypercortisolism in Patients with Early Untreated Rheumatoid Arthritis. Journal of Clinical Endocrinology and Metabolism 82(4):1279-1283, 1997.
Cutolo et al. "Circadian Rhythms and Arthritis," Rheum Dis Clin Nam 31:115129. 2005.
Cutolo et al., •circadian Rhythms in RA Rheumatoid Arthritis. 62:593-596,.2003.
Cutolo et al. circadian melatonin and cortisol levels in rheumatoid arthritis patients in winter time: a north and south Europe Comparison • Ann Rheum Dis 64:212216 (2005).
Da Silva et al, Safety of tow Dose Glucocorticoid Treatment in Rheumatoid Arthritis: Published Evidence and Prospective Trial Data: Ann Rheum Dis 65:285-293, 2006.
Deltasone Prednisone Tablet label Aug. 2006 7 pages.
Fukui et al., "Studies on Applicability of Press-Coated Tablets Using Hydroxypropyl-cellulose (HPC) in the Outer Shell for Time-Release Preparation." J. Controlled Release 68:215-223.

(56) References Cited

OTHER PUBLICATIONS

Garnero et al., Association of baseline levels of markers of bone and cartilage degradation with long term progression of joint damage in patients with early rheumatoid arthritis, Arthritis Rheumatism 46(111:2847 {2002}.
Gellner et al, "CRH Test Prior to Discontinuation of Long-Term Low dose Glucocorticoid Therapy." Exp Clin Endocrinol Diabetes 107:1999-561-7.
Groch, Delayed-Release Prednisone Works for Morning Stiffness In RA: Med Page Today Jan. 18, 2008.
Guobjornsson et al., Intact Adrenocorticotropic Hormone secretion but impaired Cortisol Response in Patients with Active Rheumatoid Arthritis. Effect of Glucocorticoid ; Journal of Rheumatology 23(4):596-602. 1996.
Guidance for Industry "Clinical Development Programs for Drugs, Devices and Biological Products for the Treatment of Rheumatoid arthritis (RA)." FDA 'Feb. 1999.
Heshmati et at., "Effects of the Circadian Variation in serum Cortisol in Markers of Bone Turnover and Calcium Homeostasis in Normal Postmenopausal Women," J of Clinical Endocrinology and Metabolism 83(3):751 756.
Hewlett et al ,Outcome Generated by Patients with Rheumatoid Arthritis:1-iOW Important Are They? Musculoskeletal Care 3: 131-142 2005.
Hickling et at, "Joint Destruction After Glucocorticoids Withdrawn in early Rheumatoid Arthritis." British J. ofRheumato100v 37:930-936, 1998.
Hoppe, The Evaluation of Iodinated Organic Compounds as Radiopaque Media. 1959, Journal of the American Pharmaceutical Association, vol. XLVIII No. 7 pp. 368-379.
http://www.eliz.com/Hata/ht..aP55.php; website reference for the tablet compressor used in the reference; downloaded Jul. 26, 2012.
http: www.equipnet.com/kilian-rud-120-20-Station-rotary.;ta ss-d-size-tcioling.Jistid.:312567; website reference for the dry coating compressor used in the reference:downloaded:Jul. 26, 2012.
http:flwww.onlineconversion.com; website download showing the conversion of compression force units; downloaded Jul. 26, 2012.
Hudson et al., "Morning Stiffness Is a Better Predictor of Function in early Inflammatory Arthritis than Are Swollen and Tender Joints," McGill Early Arthritis Research Group; McGill university, Montreal PQ. Program No. 1036.
Jacobs et al., "Follow-up Radiographic Data on Patient and with Rheumatoid Arthritis Who participated in a Two-Year Trial of Prednisone Therapy or Placebo," Arthritis:& Rheumatism 54(5):14221428, May 2006.
Jacobs .et al. "Modified Release Prednisone in Patients with Rheumatoid Arthritis." Ann Rheum Dis 2010: 4 pages.
Karatay et al., "The timing of low dose glucocorticoid therapy in treatment of rheumatoid arthritis"; The Pain Clinic vol. 13 No. 4 2002 00; 305'-312.
Kirwan et al., "Effects of Glucocorticoids on Radiological Progression of Rheumatoid Arthritis (Review)" The Cochrane Library 1:1 68 2007.
Kirwan et al, Glucocorticoids Strongly Suppress Joint Damage in Rheumatoid Arthritis: a Meta-analysis of 1,414 Patients in 15 Trials; OASIS—Online Abstract Submission and Invitation System TM 1996-2005 Coe-Truman Technologies Inc.
Kirwan et al., "Effects of Glucocorticoids on Joint Damage in Rheumatoid Arthritis," The Arthritis and Rheumatism Council Low-Dose Glucocorticoid Study Group, N. Eng J Med 333: 142-146 (1995).
Leloet X et at, Clinical Practice Decision Tree for the Choice of first disease Modifying Antirheumatic Drug for Very Early Rheumatoid Arthritis: A 2004 Proposal for the French Society of Rheumatology, Annals of Rheum Dis 65:45-50 (2006).
Lin el al., Compression Forces and Amount of Outer Layer affecting the time Controlled Disintegration of the Compression-Coated Tablets Prepared by Direct Compression With Micronized Ethylcellulose. J. Pharma. Sci. 90.12(2001):2005-2009.
Lin et al., Micronized Ethylcellulose Used for Designing a Directly Compressed Time-Controlled Disintegration Tablet J. Controlled Release, 70, 321-328 (2001).
Lin et al. "Influence of Excipients, Drugs, and Osmotic Agent in the Inner Core on the Time-Controlled Disintegration of Compression-Coated Ethylcellulose Tablets." J. Pharm. Sci. 91(9), 2040-2046 (2002).
Lin et al, "Current status and approaches to developing press-coated chronodelivery drug systems," J. Controlled Release 157, 331-353 (2012).
Lin et al., "Preparation and evaluation of sodium diclofenac controlled-release tablets II. Dibasic calcium phosphate as a retardant in mixtures for direct compression," Pharmacy World & Science 17(2) 42-47 (1995).
Mastorakos et al., "Relationship Between Interleukin-6; (IL-6) and Hypothalamic-Pituitary-Adrenal Axis Hormones in Rheumatoid Arthritis." Z Rhematol 591Si.1Do 2\:11116-1t119: 2000.
Mastorakos et al., "Recombinant Interleukin-6 Activates the Hypothalamic-Pituitary-Adrenal Axis in Humans." J Clin Endocrinol Metab 77; 1993 1690-4.
Nichols et al.,Diurnal Variation in Suppression of Adrenal Function by Glucocorticoid, J Clin Endocr 25; 1965: 343-9.
Nishimoto .et al., Interleukin 6; from Bench to Bedside, Rheumatology, 2(11): 619-626,2006.
Perry et al., Overnight Variations in Cortisol; Interleukin 6. Tumor Necrosis Factor 8 and other Cytokines in People with Rheumatoid Arthritis. Ann Rheum Dis 68: 2009, 63-68.
Peters et at "A Review of the Prevalence, disease burden and options for treatment. Respiratory Medicine 100: 1139"-1151 (2006).
Pincus et al. "Patients Seen for Standard Rheumatoid Arthritis Care Have Significantly better Articular, Radiographic, Laboratory, and Functional Status in 2000 Than in 1995," Arthritis & Rheumatism American college of Rheumatology 52(4):1009-1019, Apr. 2005.
Prednisone Tablet Label; Apr. 2008. 11 pages.
Prednisone Tablets USP Label Oct. 2007 2 pages.
Prokein R. (Doctoral Thesis), E. Merck Darmstadt, Germany, 1982.
Saag. et al., "Low dose long-term Corticosteroid Therapy in Rheumatoid Arthritis: An analysis of serious adverse events," The American Journal of Medicine 96:115-123, Feb. 1994.
Saag et al., "Low-Dose Corticosteroids in Rheumatoid Arthritis—A Meta-Analysis of Their Moderate-Term Effectiveness," Arthritis Rheum 39• 1996• 1818-25.
Schmidt et al. "Calcium Phosphates in Pharmaceutical Tableting." Pharm. World Sci. 15.3(1993):105-115.
Sinclair, "Treatment of Rheumatic Disorders with Special Reference to Akylosing Spondylitis," Proc. Royal Soc. Med. vol. 64, 1971 p. 39-46.
South African Electronic Package Inserts, Prednisone Tablets, 1998, htto:/Jhome.intekom. com/oharm/lennon/orednson.html, pp. 1-2.
Stedman's Dictionary entry for term "refractory".
Strand et al.; Clin Exp Rheumatology (2003); 21 (Suppl 31), S186-S.190.
Straub et al., Circadian Rhythms in Rheumatoid Arthritis: Implications for Pathophysiology and Therapeutic Management, Arthritis & Rheumatism 56(2):399408. 2007.
Stucki et al., "The International Classification of Functioning, Disability and Health (ICF) Core Sets for Rheumatoid Arthritis: A Way to Specify Functioning." Ann Rheum Dis 63 (Suppl 2); 2004, 40-5.
Sutherland et al., Nocturnal asthma: Journal of Allergy and Clinical Immunology 116(6}: 1179-1186 (2005).
Svensson et al., Low-Dose Prednisolone in Addition to .the Initial Disease Modifying Antirheumatic Drug in Patients with Early Active Rheumatoid Arthritis Reduces Joint Destruction and Increases the Remission Rate ,.Arthritis & Rheumatism 52( 11}:3360-3370, Nov. 2005.
Tembo et al., Effect of food on the bioavailability of prednisone,• The Journal of Clinical Pharmacology. Nov.-Dec. 1976).
Uribe et al. Gastroenterology 71:362 (1976).
Update of the Clinical Practice Guideline for the Management of Rheumatoid Arthritis in Spain (2007).

(56) References Cited

OTHER PUBLICATIONS

Van Everdingen et al., "Low-Dose Prednisone Therapy for Patients with Early Active Rheumatoid Arthritis: Clinical Efficacy, Disease-modifying Properties, and Side Effects." Annals of Internal Medicine 136'1): 1-12. Jan. 1, 2002.
Van Staa et al., Oral Corticosteroids and Fracture Risk: Relationship to Daily and Cumulative Doses, Department of Pharamacoepidemiology and. Pharmacotherapy, University of Utrech, Sorbonnelaan 16 Utrecht. The Netherlands Rheumatology 29; 1383-1389, 2000.
Wassenberg et al., "Very Low-dose Prednisolone in Early Rheumatoid Arthritis Retards Radiographic Progression over Two Years," Arthritis & Rheumatism, American College of Rheumatology 52(11):3371-3380 Nov. 2005.
Website reference for Eudragit (http:/leudragit,evonik.com/product/eudragit/en/products.. services/eudragit-products/pages/default.aspx).
Zlatkina, "The Modem Therapeutic Tactics of inflammatory Bowel Disease Consilium Medicum." Gastroenterology. 6{1}.(2004). (http:l/www.consiliurnmedicum.com/maQazines/magazines/cm/gastro/article/7275).
Physician's Desk Reference, 49th Ed. (1995), p. 2137.
Physician's Desk Reference, 50th Ed. (1996), p. 2242.
Martindale: The Extra Pharmacopoeia, 29th Ed. (1989)pp. 898, 900.
Correspondence of Arnold Bloom, British Medical Journal, p. 766-767 (1961).
[Present-day Therapeutic medicine], Feb. 1992, 21th Version, p. 195 (translation from Japanese).
International Application No. PCT/EP2007/006894 International Search Report dated Jan. 16, 2008.
International Application No. PCT/EP2007/006894 Written Opinion dated. Feb. 3, 2009.
International Application No. PCT/IB2004/001693 international Search Report dated Oct. 21, 2004.
International Application No. PCT/IB2004/001702 International Search Report dated Oct. 18, 2004.
U.S. Appl. No. 10/554,258, Office Action dated Jun. 22, 2010.
U.S. Appl. No. 10/554,258, Office Action dated Jan. 18, 2011.
U.S. Appl. No. 10/554,258 Office Action dated Sep. 19, 2011.
U.S. Appl. No. 10/554,258, Office Action dated Dec. 29, 2011.
U.S. Appl. No. 10/554,258, Office Action dated Jun. 5, 2012.
U.S. Appl. No. 10/554,258, Office Action dated Dec. 19, 2010.
U.S. Appl. No. 10/554 538 Office Action dated Nov. 23, 2010.
U.S. Appl. No. 10/554,538 Office Action dated Sep. 30, 2011.
U.S. Appl. No. 10/554,538 Notice of Allowance dated Mar. 19, 2012.
U.S. Appl. No. 11/216,469 Office Action dated Mar. 19, 2009.
U.S. Appl. No. 11/216,469 Office Action dated Dec. 23, 2009.
U.S. Appl. No. 11/216,469 Advisory Action dated Jun. 22, 2010.
U.S. Appl. No. 11/216,469, Office Action dated Mar. 1, 2011.
U.S. Appl. No. 11/833,322 Office Action dated Apr. 16, 2010.
U.S. Appl. No. 11/833,322, Office Action dated Aug. 20, 2010.
U.S. Appl. No. 11/833,322 Office Action dated. Aug. 2, 2011.
U.S. Appl. No. 11/833,322 Office Action dated Nov. 29, 2011.
U.S. Appl. No. 11/833,322 Advisory Action dated Mar. 13, 2012.
U.S. Appl. No. 12/697,384, Office Action dated Dec. 21, 2011.
U.S. Appl. No. 12/697,384, Office Action dated Sep. 11, 2012.
U.S. Appl. No. 12/693,565. Office Action dated Feb. 13, 2013.
U.S. Appl. No. 13/421,135; Office Action dated Jul. 31, 2012.
U.S. Appl. No. 13/421,135, Office Action dated Dec. 2Q, 2012.
U.S. Appl. No. 13/428,548. Office Action dated Jul. 17, 2012.
U.S. Appl. No. 13/428,548. Notice of Allowance dated Feb. 1, 2013.
U.S. Appl. No. 13/860,015, Office Action Dated Mar. 24, 2014.
UK Patent Application No. GB 0309342.4, Search Report dated Aug. 22, 2003.
UK Patent Application No. GB 0309342.4, Search Report dated Oct. 23, 2003.
U.S. Appl. No. 13/791,816. Office Action dated Dec. 16, 2013.
U.S. Appl. No. 12/693,565. Office Action dated Dec. 17, 2013.
U.S. Appl. No. 10/554,258, Office Action dated Dec. 19, 2012.
U.S. Appl. No. 10/554,258, Office Action dated Jul. 24, 2013.
Translation of WO 01/68056. Made on Feb. 6, 2013.
US Prescribing Information for Rayos, Jul. 2012.
European Summary of Product Characteristics for Lodotra, Mar. 16, 2009.
Clinical Review, Center for Drug Evaluation and Research Application No. 202020Orig1s000, review completion date Jun. 20, 2012.
Clinical Pharmacology and Biopharmaceutics Review(s), Center for Drug Evaluation and Research Application No. 202020Orig1s000, review submission date Sep. 26, 2011.
Guidance for Industry, Food-Effect Bioavailability and Fed Bioequivalence Studies, U.S. Department of Health and Human Services, Food and Drug Administration, Center for Drug Evaluation and Research (CDER), Dec. 2002.
Complaint, *Horizon Pharma AG et al. -v- Watson Laboratories, Inc.—Florida, et al.*, U.S. District Court for the District of New Jersey, Civ. Action No. pending (Aug. 26, 2013).
Watson Laboratories, Inc. "Detailed Factual and Legal Bases for WLF's Paragraph IV Certifications That the Claims of U.S. Patents Nos. 6,488,960; 6,677,326; 8,309,124; 8,168,218; and 8,394,407 are Invalid, Unenforceable, and/or Not Infringed." Jul. 15, 2013.
*Horizon Pharma AG and Jagotec AG v. Watson Laboratories, Inc. Florida, Actavis Pharma, Inc., Andrix Corporation, and Actavis, Inc.* Complaint for Patent Infringement and Exhibits A-E. Aug. 26, 2013.
Defendant Watson Laboratories, Inc.—Florida's Answer, Separate Defenses, and Counterclaims to Plaintiffs Complaint in the case of *Horizon Pharma AG and Jagotec AG v. Watson Laboratories, Inc—Florida.* (Civil Action No. 13-5124 (JEI/JS)) dated Nov. 12, 2013.
Plaintiffs Horizon Pharma AG and Jagotec AG's Answer to Counterclaims of Watson Laboratories, Inc.—Florida in the case of *Horizon Pharma AG and Jagotec AG v. Watson Laboratories, Inc.—Florida.* (Civil Action No. 13-5124 (JEI/JS)) dated Dec. 13, 2013.
Report on the Filing or Determination of an Action Regarding a Patent or Trademark in the case of *Horizon Pharma AG v. Watson Laboratories, Inc—Florida.* (Civil Action No. 13-5124 (JEI/JS)) dated Aug. 27, 2013.
Invalidity Contentions, *Horizon Pharma AG et al. -v- Watson Laboratories, Inc.—Florida, et al.*, U.S. District Court for the District of New Jersey, Civ. Action No. (Civil Action No. 13-5124 (JEI/JS)) May 13, 2014.

* cited by examiner

DELAYED-RELEASE GLUCOCORTICOID TREATMENT OF RHEUMATOID DISEASE

This application is a continuation of U.S. application Ser. No. 13/860,015, filed Apr. 10, 2013, which is a continuation of U.S. application Ser. No. 13/176,598, filed Jul. 5, 2011, which is continuation of U.S. application Ser. No. 11/833,322, filed Aug. 3, 2007, which claims the benefit of U.S. Provisional Application No. 60/835,093, filed Aug. 3, 2006, the contents of each of which are hereby incorporated by reference as if written herein in their entireties.

The present invention refers to the treatment of a rheumatic disease and/or osteoarthritis by administering a delayed-release dosage form of a glucocorticoid to a subject in need thereof.

BACKGROUND OF THE INVENTION

Role of Low-Dose Corticoid Therapy in Clinical Practice

Diseases of rheumatoid nature like rheumatoid arthritis (RA) are chronic, autoimmune disorders in which inflammation of the synovial joint lining is accompanied by joint pain and stiffness and usually leads to bone and joint destruction, deformity, disability, and even death. RA affects about 1% of the population and is 2 to 3 times more common in women than in men (CPMP/EWP/556/95). Early diagnosis, suppression of inflammation, and aggressive treatment strategies are regarded as important requisites for a favorable outcome (Pincus 2005). Glucocorticoids are widely used to treat the disease and are often administered in combination with other drugs, especially disease-modifying antirheumatic drugs (DMARDs) and non-steroidal anti-inflammatory drugs (NSAIDs) (Bijlsma 2003). Prednisone, prednisolone and methylprednisolone are among the most common glucocorticoids for the treatment of RA.

Use and types of oral corticoid RA therapy differ according to region and published estimates vary. According to one source, in 2002 about 40 to 50% of patients in France, Germany, Italy and Spain received such therapy compared to about 20% in the United Kingdom (UK). Prednisone was the most common corticoid in France, Italy and Spain (94%, 59% and 43% of treated patients, respectively) whereas prednisolone was the most common in Germany and the UK (50 and 100%, respectively). A study in 150 patients who attended a US clinic during the period 1999 to 2001 showed that 144 (96%) patients took prednisone in combination with DMARDs (86%) or alone (10%) (Pincus 2005).

Glucocorticoids have a broad spectrum of anti-inflammatory and immunosuppressive effects. They act by inhibiting leukocyte traffic; interfering with functions of leukocytes, fibroblasts, and endothelial cells; and suppressing the synthesis and actions of inflammatory cytokines including interleukin-6 (IL-6) (Buttgereit 2005). When they were first introduced, glucocorticoids were administered to RA patients for long periods at high doses exceeding 10 mg/day prednisone or equivalent. These high-dose, long-term regimens were highly effective but were associated with pleiotropic effects and unacceptable adverse reactions. This led to the development of low-dose regimens in order to reduce the incidence of side effects and optimized the benefit:risk ratio (Buttgereit 2005). High corticoid doses are now only considered suitable for short-term therapy in special cases (e.g. for treatment of a severe flare of RA). Decreases in prescribed corticoid dose are illustrated by an evaluation of patients who attended a US clinic between 1984 and 1986 (1985 cohort) or between 1999 and 2001 (2000 cohort) (Pincus 2005). The mean prednisone dose was 7.8 mg/day in 1985 compared to 4 mg/day in 2000, with median doses of 5 and 4 mg/day, respectively.

Long-term, low-dose, corticoid therapy (defined as daily doses of ≤10 mg prednisone or equivalent) is currently recognized as an important part of standard treatment for RA (ACR guideline, Conn 2001). Below 10 mg the daily dose should be decreased stepwise until the lowest, still effective dose for disease control is reached. In addition to providing immediate relief of symptoms such as morning stiffness and pain, the low-dose corticoid regimen also prevents progression of disease. Several randomized studies performed since the mid-1990s have shown that low-dose prednis(ol)one slows the rate of joint damage (as measured by radiographic images) in patients with early, active RA. In a double-blind, placebo-controlled study, 7.5 mg/day prednisolone reduced joint destruction when given for 2 years in combination with other standard RA treatments (Kirwan 1995). When prednisolone was stopped, joint destruction returned to the same level as in the control group (Hickling 1998). In a more recent double-blind, placebo-controlled study, prednisone (10 mg/day) slowed progression of joint damage over periods of 2 and 5 years in patients who had not been pretreated with DMARDs (van Everdingen 2002, Jacobs 2005). In a double-blind, placebo-controlled study (Wassenberg 2005) and an open-label, DMARD-controlled study (Svensson 2005), prednisolone at doses of 5 and 7.5 mg/day, respectively, decreased radiographic progression when given in combination with DMARDs for 2 years. The increasing evidence for the disease-modifying effects of low-dose corticoid treatment has certainly contributed to renewed interest in this treatment regimen and increased use in clinical practice.

Safety of Low-Dose Long-Term Corticoid Therapy

Soon after glucocorticoids were introduced for the treatment of RA in the 1950s it became apparent that long-term use of high doses was associated with clinically significant side effects that included osteoporosis, glucose intolerance, infections, peptic ulcers and gastrointestinal bleeding, cataracts and glaucoma, as well as atherosclerotic disease. Several clinical studies and literature reviews have been performed to assess the safety profile of low-dose, long-term corticoid therapy. It is generally agreed that side effects can be reduced by using as low a dose as possible for each individual patient. One study that compared RA patients with and without prednisone treatment concluded that long-term prednisone use at doses ≥5 mg/day was associated with the dose-dependent development of specific AEs (Saag 1994). However, this study was retrospective with historical case controls and included prednisone doses up to 15 mg/day. A working group of rheumatologists and experts from other therapeutic areas has recently conducted a comprehensive literature review of the adverse effects of low-dose (10 mg/day prednisolone equivalent), long-term glucocorticoid therapy by a primary search of textbooks and review papers (da Silva 2006). Their review also included analysis of data from 4 prospective, randomized, controlled studies in which prednisolone (5 to 10 mg/day) was given to RA patients for 2 years (Capell 2004, Kirwan 1995, van Everdingen 2002, Wassenberg 2005). Common side effects seen at high doses were not observed at low doses or were less frequent. The experts concluded that "the overall fear of glucocorticoid toxicity in RA, as quoted in textbooks and review articles, is probably overestimated based on observations with higher dose therapy. The balance of risks and benefits of low-dose therapy clearly differs from that of medium- and high-dose therapy . . . ". Osteoporosis, obesity, hypertension, family history of diabetes or glaucoma were listed as risk factors requiring more careful observation. In addition to osteoporosis, adverse effects that may need regular checks were defined as Cushingoid syndrome, adrenal crisis of corticoid withdrawal, new onset of diabetes mellitus, worsening of glycemia control in patients with diabetes mellitus, cataracts, glaucoma, peptic ulcer (in combination with NSAIDs), and hypertension.

Delayed-Release Prednisone Tablets

Patients with active RA suffer from clinical signs and symptoms that include joint stiffness, pain, and swelling. Patients have assessed these symptoms (and related factors such as disability and mobility) as being important outcomes of RA treatment (Ahlmen et al. 2005, Carr et al. 2003, Hewlett et al. 2005). Clinical symptoms vary during the day and are more severe early in the morning after awakening than in the afternoon or evening (Cutolo et al. 2003, Cutolo and Masi 2005). Indeed, morning stiffness is such a typical symptom of RA that it has become a standard diagnostic criterion for the disease (Arnett et al. 1988, ACR Guideline 2002).

The mechanisms responsible for the circadian variation of RA symptoms are complex and involve the HPA axis and endogenous inflammatory mediators. Inflammation causes increased production of inflammatory cytokines. In comparison with healthy subjects, RA patients therefore have higher serum concentrations of interleukins (IL), especially IL-6, and tumor necrosis factor-alpha (TNFα) and levels display a pronounced circadian rhythm, with higher night-time concentrations that peak at 02:00 to 06:00 (Arvidson et al. 1994; Crofford 1997; Cutolo 2003, 2005).

Increased levels of IL-6 are produced in response to inflammation but IL-6 is a potent activator of the HPA axis and stimulates the release of cortisol from the adrenal cortex to counteract the inflammation (Cutolo 2005, Mastorakos 2000). In RA patients, it seems that the response of the permanently stimulated HPA axis is inadequate and levels of endogenous cortisol are insufficient to combat the inflammation (Gudbjornsson 1996). Administration of exogenous glucocorticoids acts—among other therapeutic effects—as a replacement therapy and supplements the inadequate levels of endogenous cortisol (Cutolo 2005).

Endogenous cortisol and exogenous therapeutic glucocorticoids inhibit the synthesis of IL-6 and other pro-inflammatory cytokines. In this context, prednis(ol)one and methylprednisolone are ideally suited exogenous corticoid due to its comparatively short half-life of 3-4 h. Low-dose oral prednis(ol)one or methylprednisolone are usually given for symptomatic relief as a single morning dose to minimize potential interference with the HPA axis. However, in order to provide optimal relief of morning stiffness and joint pain it has been proposed that the drug should be given shortly before the expected nocturnal increase of IL-6. A randomized study has investigated the efficacy of standard IR (Immediate Release) low-dose prednisolone (5 or 7.5 mg/day) given at 02:00 or at 07:30 for 4 days in 26 patients with active RA who were being treated with standard anti-rheumatic drugs (predominantly NSAIDs) but who had not received glucocorticoids in the 3 months before the study (Arvidson et al. 1997). Night-time administration of prednisolone at 02:00 resulted in highly statistically significant improvements in morning stiffness, joint pain, as well as suppression of serum concentrations of IL-6 (p<0.01). Much smaller effects (p<0.05) were only observed for morning stiffness and IL-6 concentrations after conventional morning dosing at 07:30. The authors concluded that low doses of glucocorticoids improved acute RA symptoms if they were administered before the circadian flare of increased IL-6 synthesis and inflammatory activity. However, it remained unclear what would happen to the patients if they would be treated for a longer period of time.

Karatay et al investigated in 2002 the administration of an IR low-dose prednisone tablet over a period of 6 months at 02:00 vs 07:30. The results were disappointing because a difference in morning stiffness could not be observed. One explanation of this could be that the short term effects observed by Arvidson disappear after several days or weeks of therapy. Thus, the effects on long term night time administration of glucocorticoids remained unclear.

Furthermore, all patients in both study (Arvidson 1997; Karatay 2002) were corticoid naive. Thus, the question has arisen, how low-dose night-time prednisone would work in patients already pre-treated with low-dose corticoids and what would happen if they would get the night-time dose over a longer time with a higher compliance rate.

Although administration of glucocorticoids at 02:00 resulted in improved efficacy in one of two studies, in practice this would be highly inconvenient for the patient and likely to result in poor quality of sleep and/or compliance.

U.S. Pat. No. 5,792,476 describes a pharmaceutical composition for peroral administration for rheumatoid arthritis, which comprises a glucocorticoid as active ingredient and which leads to release in the small intestine. The composition is a granulate which is laminated with an inner layer which is resistant to a pH of 6.8, and with an outer layer which is resistant to a pH of 1.0.

U.S. Pat. No. 6,488,960 describes a pharmaceutical dosage form for controlled release of corticoids, reference being made to the formulations described in U.S. Pat. No. 5,792,476.

WO 01/08421 describes a tablet having a core which is coated by at least two layers, one of which completely encloses the other. The coating layers can be produced by spray coating and/or pressing.

WO 01/68056 discloses a pharmaceutical preparation having a release profile with a time delay, comprising a core and at least one hydrophilic or lipophilic coating surrounding the core, where the coating is slowly swollen, dissolved, eroded or changed in its structure in another way through the water present in the release medium, so that the core or parts of the core become accessible to the release medium. The coating may be formed for example as pressed coating.

WO 02/072034 discloses a pharmaceutical dosage form for delayed release, having a core which comprises as active ingredient a glucocorticoid and a material which brings about delayed release and includes at least one natural or synthetic gum.

WO 2004/093843 discloses a tablet with a specific core geometry to release the active ingredient in a specific delayed release manner.

WO 2006/027266 discloses a pharmaceutical dosage form with site- and time controlled gastrointestinal release of an active agent, particularly a corticosteroid. The pharmaceutical dosage form is preferably a coated tablet having a core comprising the corticosteroid and a swellable/disintegration adjuvant, and an inert outer coating. The coating is compressed at a pressure chosen to result in the release of the corticosteroid at a predetermined position in the gastrointestinal tract.

SUMMARY OF THE INVENTION

The present inventors have carried out a clinical study in order to test the efficacy of a delayed-release prednisone tablet compared to a standard immediate-release tablet. It was found that long-term administration of the delayed-release prednisone tablet shows a surprisingly increased efficacy compared to the treatment with a standard immediate-release prednisone tablet.

Thus, a first aspect of the invention refers to the use of a delayed-release dosage form of a corticosteroid for the manufacture of a medicament for the long-term treatment of a rheumatic disease and/or osteoarthritis.

A further aspect of the invention refers to the use of a delayed-release dosage form of a glucocorticoid for the manufacture of a medicament for the treatment of a rheumatic disease and/or osteoarthritis in
(i) patients with severe diseases,
(ii) patients with moderate diseases,
(iii) patients with mild diseases,
(iv) patients with short disease duration (<2 years),
(v) patients with mid-term disease duration (2-5 years) or
(vi) patients with long-lasting disease duration (>5 years).

Still a further aspect of the present invention refers to the use of a delayed-release dosage form of a glucocorticoid for the manufacture of a medicament for the treatment of a rheumatic disease and/or osteoarthritis in
(i) patients with severe, long lasting morning stiffness
(ii) patients with moderate morning stiffness;
(iii) patients with mild morning stiffness;
(iv) patients with severe, long lasting pain
(v) patients with moderate pain;
(vi) patients with mild pain.

Still a further aspect of the present invention refers to the use of a delayed-release dosage form of a glucocorticoid for the manufacture of a medicament for the treatment of a rheumatic disease and/or osteoarthritis in
(i) patients with high Interleukin 6 levels;
(ii) patients with medium Interleukin 6 levels or
(iii) patients with low Interleukin 6 levels.

Still a further aspect of the present invention is the use of a delayed-release dosage form of a glucocorticoid for the manufacture of a medicament for the treatment of a rheumatic disease and/or osteoarthritis in
(i) patients who have been pre-treated with an immediate release dosage form of a glucocorticoid,
(ii) patients who are refractory to treatment with an immediate release dosage form of a glucocorticoid, or
(iii) glucocorticoid naive patients.

Still a further aspect of the present invention refers to the use of a delayed-release dosage form of a glucocorticoid for the manufacture of a medicament for the treatment of rheumatic diseases in
(i) patients who have been pre-treated with other medicaments like a NSAID, a DMARD, a TNFα inhibitor, an IL-6 inhibitor and/or an analgetic agent or any combination thereof, or
(ii) patients who have not been pre-treated with any other medicaments like a NSAID, a DMARD, a TNFα inhibitor, an IL-6 inhibitor and/or an analgetic agent.

Still a further aspect of the present invention refers to the use of a delayed-release dosage form of a glucocorticoid for the manufacture of a medicament for the treatment of a rheumatic disease and/or osteoarthritis in combination with at least one further medicament which is a NSAID, a DMARD, a TNFα inhibitor, an IL-6 inhibitor and/or an analgetic agent.

Still a further aspect of the present invention is the use of a delayed-release dosage form of a glucocorticoid for the manufacture of a medicament for the treatment of a rheumatic disease and/or osteoarthritis without any further medicament.

Still a further aspect of the present invention is the use of a delayed-release dosage form of a glucocorticoid for the manufacture of a medicament for treatment of a rheumatic disease and/or osteoarthritis in combination with reduced doses of at least one further medicament which is a NSAID, a DMARD, a TNFα inhibitor, an IL-6 inhibitor and/or an analgetic agent.

Still a further aspect of the present invention is the use of a delayed-release dosage form of a glucocorticoid for the manufacture of a medicament for the treatment of ankylosating spondylitis, polymyalgia rheumatica and/or osteoarthritis.

Still a further aspect of the present invention is the use of a delayed-release dosage form of a glucocorticoid for the manufacture of a medicament for the treatment of morning stiffness, pain and/or inflammation parameters such as release of cytokines, e.g. in a rheumatic disease and/or osteoarthritis.

Still a further aspect of the present invention is a method for the treatment of a patient suffering from signs and symptoms of an underlying rheumatic disease and/or osteoarthritis, which comprises administering to said patient an effective amount of a glucocorticoid contained in a delayed-release dosage form, wherein said treatment is administered once daily for at least about two weeks.

Still a further aspect of the present invention is a method for the treatment of a patient suffering from morning stiffness and pain due to an underlying rheumatic disease and/or osteoarthritis, which comprises administering to said patient an effective amount of a glucocorticoid contained in a delayed-release dosage form, wherein said treatment is administered once daily for at least about two weeks.

Still a further aspect of the present invention is a method for the treatment of a patient having circadian fluctuations in Interleukin 6 levels due to underlying inflammation, which comprises administering to said patient an effective amount of a glucocorticoid contained in a delayed-release dosage form, wherein said treatment is administered once daily for at least about two weeks, and wherein said treatment is administered such that the glucocorticoid is released at or before the time when the patient's Interleukin 6 level is at a daily peak.

DETAILED DESCRIPTION OF THE INVENTION

Figure 1:
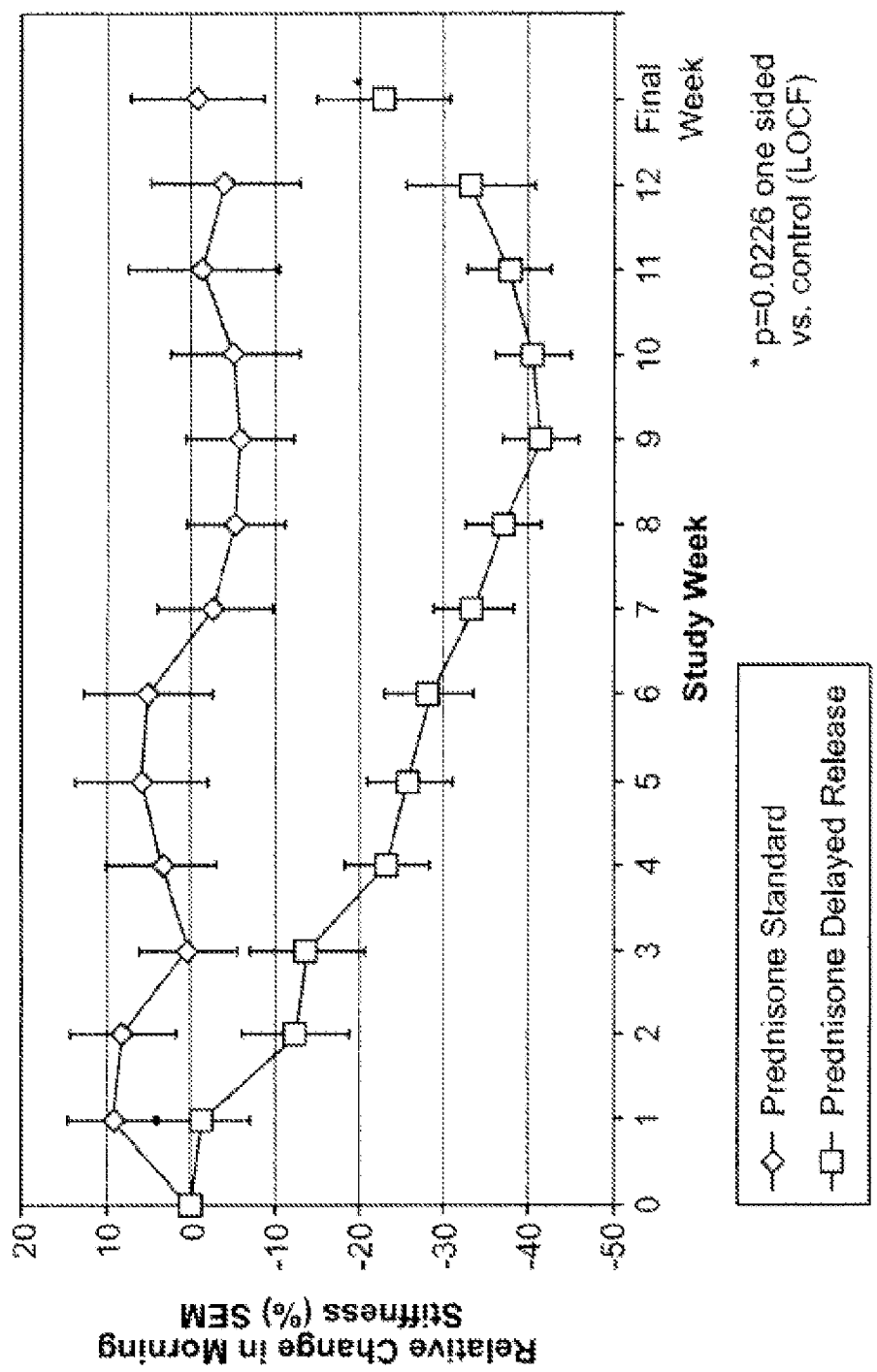
FIG. 1 shows duration of Morning Stiffness: Relative Change from Baseline in % (SEM) per week of treatment in the ITT population.

The present invention refers to the use of a delayed-release dosage form of a glucocorticoid. The release of the active ingredient is preferably delayed for a time period of 2-10 hours after intake, preferably 2-6, more preferably 3-5 hours after intake the active ingredient may be released in the upper sections of the intestine and/or in the lower sections of the intestine. More preferably, the active ingredient is released in the upper sections of the intestine within a period of 2-6 hours. The delayed-release dosage form is preferably administered to the patient at or before bedtime, more preferably in the evening, e.g. from about 9:00 pm to about 11:00 pm. Because inflammation is accompanied with circadian fluctuations in the concentration of pro-inflammatory cytokines (such as Interleukin-6) which peaks during sleeping hours, bedtime administration allows an efficacious concentration of the active ingredient to be present when such concentration peaks.

The delayed-release dosage form is preferably a tablet, e.g. as described in WO 2006/027266, which is herein incorporated by reference. The dosage form preferably comprises (a) a core having at least one glucocorticoid-active ingredient and having at least one swellable adjuvant and/or a disintegrant such that the active ingredient is rapidly released from the dosage form when the core is contacted with gastrointestinal fluids, and
(b) an inert, e.g. a non-soluble and non-swellable coating pressed onto the core, said coating being capable of preventing substantial release of the active ingredient for a defined time period following ingestion of the dosage form.

The inert coating initially prevents release of the active ingredient or the active ingredient combination over an exactly defined period, so that no absorption can occur. The water present in the gastrointestinal tract penetrates slowly in through the coating and, after a time which is previously fixed by the pressure for compression, reaches the core. The coating ingredients show neither swelling nor diluting of parts of the coating. When the core is reached, the water penetrating in is very rapidly absorbed by the hydrophilic ingredients of the core, so that the volume of the core increases greatly and, as a consequence thereof, the coating completely bursts open, and the active ingredient and the active ingredient combination respectively is released very rapidly.

A particularly advantageous embodiment of this press-coated delayed-release tablet is achieved when a previously compressed core tablet is subsequently compressed with a multilayer tablet press to a press-coated tablet.

The tablet coating typically consists of the following materials in order to achieve a delayed release profile:
polymer or copolymer of acrylic acid, methacrylic acid etc. (e.g. Eudragits or Carbopol),
cellulose derivatives such as hydroxypropylmethylcellulose, hydroxypropylcellulose, carboxymethylcellulose, ethylcellulose, cellulose acetate,
polyvinyl alcohol,
polyethylene glycol, salts of higher fatty acids, esters of monohydric or polyhydric alcohols with short-, medium- or long-chain, saturated or unsaturated fatty acids. Specifically, stearic acid triglycerides (e.g. Dynersan) or glycerol behenate (e.g. Compritol) are used.

In addition, further adjuvants should also be added to these materials so that the tablet coating can be compressed. Typically used here are fillers such as lactose, various starches, celluloses and calcium hydrogen phosphate or di-basic calcium phosphate. The glidant used is normally magnesium stearate, and in exceptional cases also talc and glycerol behenate. A plasticizer is often also added to the coating material, preferably from the group of polyethylene glycol, dibutyl phthalate, diethyl citrate or triacetin.

In order to achieve an optimal release profile, the tablet core must also fulfil certain tasks and exhibit certain properties. Thus, after the lag phase has elapsed, a rapid release profile is achieved if typical disintegrants are added to the inner core, which are derived for example from the group of the following substances: cellulose derivatives, starch derivatives, crosslinked polyvinylpyrrolidone. The use of a blowing agent, for example resulting from a combination of a weak acid and a carbonate or bicarbonate, may also promote rapid release. The tablet core typically consists additionally of matrix or filling ingredients (e.g. lactose, cellulose derivatives, calcium hydrogen phosphate or other substances known from the literature) and lubricant or glidant (usually magnesium stearate, in exceptional cases also talc and glycerol behenate).

The size of the core tablet preferably should not exceed 6 mm (preferably 5 mm) in diameter, because otherwise the press-coated tablet becomes too large for convenient ingestion. As a result thereof, the dosages of the active ingredients are in the range from 0.1 to 50 mg, very particularly between 1 and 20 mg.

The in vitro release profile of the dosage form according to the invention is preferably such that less than 5% of the active ingredient is released during the lag phase. After the release phase has started, preferably ≥80%, particularly preferably ≥90%, of the active ingredient is released within one hour. More preferably, the delayed-release dosage form has a dissolution time of equal to or less than about 2 hours after the lag time has been reached). The in vitro release is preferably determined using the USP paddle dissolution model in water.

The employed active ingredients are derived from the group of glucocorticoids and all show comparable physico-chemical properties. Such include cortisone, hydrocortisone, prednisone, prednisolone, methylprednisolone, budesonide, dexamethasone, fludrocortisone, fluocortolone, cloprednole, deflazacort, triamcinolone, or the corresponding pharmaceutically acceptable salts and/or esters thereof. This applies in particular to prednisone, prednisolone, methylprednisolone, budesonide, dexamethasone, fluocortolone, cloprednole, and deflazacort or the corresponding pharmaceutically acceptable salts and/or esters thereof.

In the present case of the delayed-release tablet, the following combination of core materials and coating materials has proved to be particularly suitable for achieving a time- and site-controlled release with exclusion of pH and food influences:

The coating preferably comprises:
hydrophobic, waxy substances with an HLB value of less than about 5, preferably around 2. Carnauba wax, paraffins, cetyl ester waxes are preferably employed therefor. Glycerol behenate has proved to be particularly suitable. The use of about 20-60%, in particular about 30-50%, in the coating has proved to be very advantageous;
non-fatty, hydrophobic filling materials such as calcium phosphate salts, e.g. dibasic calcium phosphate. The use of about 25-75% of these filling materials, in particular of about 40-60%, in the coating has proved to be very advantageous here;
in addition, the tablet coating preferably also consists of binders, e.g. polyvinylpyrrolidone (PVP), typically in concentrations of about 4-12%, specifically about 7-10%, and glidants such as magnesium stearate, in concentrations of about 0.1-2%, in the specific case of about 0.5-1.5%. Colloidal silicon dioxide can for example be used as flow regulator, normally in concentrations of about 0.25-1%. In addition, to distinguish different dosages, a colorant can be added to the tablet coating, preferably an iron oxide pigment in concentrations of about 0.001-1%.

The core tablet preferably comprises:

an active ingredient or an active ingredient combination from the group of glucocorticoids, preferably prednisone, prednisolone, methylprednisolone, budesonide, dexamethasone, fludrocortisone, fluocortolone, cloprednole, deflazacort, and triamcinolone, and the corresponding salts and esters thereof. The dosages of the active ingredients are in the region of about 0.1-50 mg, very especially between about 1 and 20 mg;

in addition, the core tablet preferably comprises a filler such as, for example, lactose, starch derivatives or cellulose derivatives. Lactose is preferably employed. The filler is typically present in concentrations of about 50-90%, specifically of about 60-80%. A disintegrant is additionally present and is typically crosslinked PVP or sodium carboxymethylcellulose, typically in concentrations of about 10-20%. It is additionally possible for a binder, e.g. PVP, to be present, typically in concentrations of about 2-10%, specifically of about 5.5-9%, and a lubricant such as magnesium stearate, in concentrations of about 0.1-2%, in the specific case of about 0.5-1.5%. Colloidal silicon dioxide is normally used as flow regulator, normally in concentrations of about 0.25-1%. It is additionally possible, for visually distinguishing the core from the coating, to add a colorant, preferably an iron oxide pigment in concentrations of about 0.01-1%.

Preferably, the delayed-release dosage form is administered as a long-term treatment to a subject in need thereof for a time sufficient to reduce and/or abolish the disease and/or disease symptoms. The long term treatment usually comprises daily administration of the medicament for an extended period of time, e.g. for at least two weeks, preferably for at least 4 weeks, more preferably for at least 8 weeks, even more preferably for at least 12 weeks, and most preferably for at least 6 months or at least 12 months.

According to the present invention refers to the novel treatment of groups of patients suffering from rheumatic diseases and/or osteoarthritis. These patient groups are selected from:
(i) patients with severe diseases characterized by a Disease Activity Score (DAS) of >5.1 (Le Loet 2006) and/or a Physicians Assessment;
(ii) patients with moderate diseases characterized by a Disease Activity Score (DAS) of >3.2 but <5.1 and/or a Physicians Assessment;
(iii) patients with mild diseases characterized by a Disease Activity Score (DAS) of <3.2 and/or a Physicians Assessment;
(iv) patients with short disease duration of less than 2 years,
(v) patients with mid-term disease duration of 2-5 years, and
(vi) patients with long-lasting disease duration of more than 5 years.

Further patient groups may be selected from:
(i) patients with severe, long lasting morning stiffness characterized by a duration of morning stiffness >180 min,
(ii) patients with moderate morning stiffness between 100 and 180 min,
(iii) patients with mild morning stiffness of less than 100 min,
(iv) patients with severe, long lasting pain characterized by a VAS scale with >70 mm,
(v) patients with moderate pain characterized by a VAS scale with >50-70 mm,
(vi) patients with mild pain characterized by a VAS scale with <50 mm.

Further patient groups may be selected from:
(i) patients with high Interleukin 6 levels, e.g. more than 3000 IU/l;
(ii) patients with medium Interleukin 6 levels, e.g. between 3000 and 1000 IU/l;
(iii) patients with low Interleukin 6 levels, e.g. less than 1000 IU/l.

Further patient groups may be selected from:
(i) patients who have been pre-treated with an immediate release dosage form of a glucocorticoid;
(ii) patients who are refractory to treatment with an immediate-release dosage form of a glucocorticoid, and
(iii) glucocorticoid naive patients.

Further patient groups may be selected from:
(i) patients who have been pre-treated with other medicaments like a NSAID, a DMARD, a TNFα inhibitor and/or an analgetic agent or any combination thereof, and
(ii) patients who have not been pre-treated with any other medicaments like a NSAID, a DMARD, a TNFα inhibitor, an Interleukin 6 inhibitor and/or an analgetic agent.

By means of administering a delayed-release tablet, the daily dose of the glucocorticoid may be substantially reduced compared to an immediate-release tablet of the glucocorticoid. Thus, the disease-inhibiting effect may be obtained by a significantly lower dose of the active ingredient, whereby the occurrence and/or intensity of site effect is diminished. For example, the daily dose of the glucocorticoid can be reduced by at least 10%, more preferably by at least 20%, e.g. by 10-50% compared to an immediate-release tablet. Thus, the reduced daily dose of prednis(ol)one in Prednisone delayed-release is preferably in the range of 1 to 5 mg/day compared to 6-10 mg/day for a standard IR tablet.

The treatment according to the present invention may comprise the treatment of a rheumatic disease and/or osteoarthritis without any further medicament. On the other hand, the invention may comprise the treatment of a rheumatic disease and/or osteoarthritis in combination with at least one further medicament which is preferably selected from the groups of NSAIDs, DMARDs, TNF a inhibitors, IL-6 inhibitors, analgetic agents or combinations thereof. Especially preferred is a combination with Tarenflurbil.

NSAIDs are preferably selected from arylalkanoic acids (Diclofenac, Indometacin, Sulindac) from 2-arylpropionic acids (Carprofen, Fenoprofen, Flurbiprofen, Ibuprofen, Ketoprofen, Ketorolac, Laxoprofen, Naproxen, Tiaprofenic acid), from N-arylanthranilic acids (Mefenamic acid, Meclofenamic acid), from Oxicams (Piroxicam, Meloxicam) or from Coxibs (Celecoxib, Parecoxib, Etoricoxib) or from combinations thereof. Especially preferred is a combination with Tarenflurbil.

DMARDs are preferably selected from gold preparations, chloroquine, azathioprine, sulfasalazine, cyclophosphamide, penicillamine, hydroxychloroquine, methotrexate, thorium dioxide suspension, levamisole, cyclosporin, interferone, leflunomide or from combinations thereof.

TNF a inhibitors and IL 1 inhibitors are preferably selected from antibodies or soluble receptors such as etanercept, inflixima, anakinra, adalimumab and from cominations thereof.

IL-6 inhibitors are preferably selected from antibodies or soluble receptors such as tocilizumab.

Analgetic agents are preferably selected from salicylates (Aspirin, Methyl salicylate, Diflunisal, Benorylate, Faislamine, Amoxiprin), from pyrazolidine derivatives (Phenylbutazone, Oxyphenylbutazone) or paracetamol or from combinations thereof.

The dose of the at least one further medicament may be substantially reduced e.g. by at least 10%, preferably by at least 20%, e.g. by 10-50%. Alternatively, the first usage of TNF a inhibitors or IL-6 inhibitors can be postponed to a later point in time.

The present invention particularly refers to the treatment of a rheumatic disease selected from rheumatoid arthritis, ankylosating spondylitis, polymyalgia rheumatica and/or to the treatment of osteoarthritis. Based on the results of the clinical trials described in the present application, it is evident that the delayed-release dosage form of a glucocorticoid, particularly a long-term treatment, is of therapeutic benefit. Particularly in the case of osteoarthritis or a rheumatic disease having an osteoarthritic component, the administration of the delayed-release dosage form is effective without having undesired side effects.

The dose of the glucocorticoid may vary during the course of treatment. For example, the patient may be administered a relatively high dose during the initiation of therapy (e.g., about 10-40 mg/day or higher of prednisone, or an equivalent amount of another glucocorticoid), which may be reduced downward over a period of time (e.g., over 3-4 weeks) according to the patient's response, to a maintenance therapy dose of about 10 mg/day or less of prednisone, or an equivalent amount of another glucocorticoid. Alternatively, the patient may be started on a relatively low dose, which may be adjusted upward over a period of time (e.g., over 3-4 weeks) to a maintenance therapy dose of about 10 mg/day or less of prednisone, or an equivalent amount of another glucocorticoid.

Further, the present invention is described in more detail by the following examples.

Example

Clinical Studies.

The clinical development program supporting the present application for the delayed-release prednisone tablet "Prednisone delayed-release" comprised 3 phase I studies and 1 phase III study:

Phase I studies: These 3 randomized, open-label, crossover studies on 69 healthy men investigated the comparative bioavailability and pharmacokinetic characteristics of 6 experimental galenic delayed-release formulations each containing 5 mg prednisone. The studies were performed to allow selection of a delayed-release tablet with appropriate characteristics for evening administration to RA patients (i.e. a suitable lag time and high bioavailability that was not affected by food). Single doses of each of the delayed-release tablets were compared to a single dose of a reference immediate release (IR) prednisone tablet (Decortin® 5 mg tablets marketed by Merck KGaA).

Phase III study: In this randomized, parallel-group, double-blind, double-dummy study on 288 adult RA patients, the final prednisone delayed-release tablet formulation was administered in the evening for 12 weeks. The daily prednisone dose of 3 to 10 mg was achieved with 1 and 5 mg tablets. Efficacy and safety were compared with the reference IR product given in the morning.

This is a novel study design which was not used by Arvidson (1997) or Karatay (2002) as patients in these studies were corticoid naive. In those studies the administration of a standard IR prednis(ol)one tablet at 2.00 and 8.00 was compared.

Study Design and Methodology

Study Design.

The studies were specifically designed to compare the efficacy and safety of Prednisone delayed-release given in the evening with standard IR prednisone (Decortin®, Merck KGaA) given in the morning at 08:00 over a period of 12 weeks. Prednisone delayed-release and the reference product both contained the same drug (prednisone) and differed solely with respect to the timepoint at which this was released in the gastrointestinal tract. Timing of the evening dose (22:00.+−.30 min) was based on results from a previous pharmacokinetic study with Prednisone delayed-release which showed first detectable plasma concentrations of prednisone and its active metabolite prednisolone after 4 hours and maximal plasma concentrations about 6 h after administration. This specific plasma profile with Cmax at 04:00 is expected to suppress the known early morning increase of pro-inflammatory cytokines, and thus reduce morning stiffness.

Inclusion of a placebo arm was not considered necessary or ethical due to the proven efficacy of prednisone. Blinding was essential in this study to avoid bias. As the Prednisone delayed-release tablets and reference product tablets differed in appearance a double-dummy technique was used to maintain the treatment blind.

The study had a 1- to 2-week screening period that was followed by a 12-week double-blind treatment period with visits after 2 and 6 weeks. This 12-week period was considered to be sufficiently long to demonstrate any differences in the primary and secondary efficacy endpoints (see below). At the end of the 12-week double blind period, patients who completed the 12-week double-blind period were offered to continue in an open-label 9-month follow up period, during which all patients received active treatment with Prednisone delayed-release.

Prednisone Dose.

Patients were to continue on the same stable low dose of prednisone (or equivalent) that they received in the month before entering the study. During the study prednisone doses of 3 to 10 mg/day were achieved with appropriate combinations of Prednisone delayed-release or IR tablets containing 1 and 5 mg prednisone; daily doses of 2.5 and 7.5 mg prednisone were rounded to 3 and 8 mg, respectively. A constant low prednisone dose was given throughout the treatment phase to ensure that any differences between the treatment groups were not due to dose changes.

Primary Objective and Efficacy Endpoint.

The primary objective of the study was to show whether administration of the new delayed-release formulation of prednisone (i.e. Prednisone delayed-release) in the evening was superior to the standard morning administration of immediate-release (IR) prednisone in reducing the duration of morning stiffness. The patient diary card was appropriately designed to capture relevant clock times in minutes: wake-up, morning medication intake, resolution of morning stiffness. The primary variable was "the relative change in duration of morning stiffness from baseline at individual study end in the double-blind treatment phase", whereby the duration of morning stiffness was the difference between the time of resolution of morning stiffness and the time of awakening. Morning stiffness was chosen as the primary variable because it was expected to be directly affected by inhibition of night-time IL-6 peaks after delayed release of prednisone.

Secondary Efficacy Endpoints.

In addition to morning stiffness, the study included a comprehensive battery of supportive secondary endpoints that were based on regulatory recommendations (CPMP/EWP/556/95 rev 1). Patients assessed their quality of sleep, pain intensity (VAS), and global disease activity (VAS). They also documented their use of analgesics and completed validated questionnaires on their health status (HAQ) and quality of life (SF36). Investigators counted the numbers of swollen and tender joints (28 joints) and assessed global disease activity (5-point scale). Laboratory variables (ESR, CRP, IL-6) were assessed from blood samples taken as early as possible in the morning to investigate the inflammatory state of the disease. Osteocalcin was also measured as an indicator of bone metabolism.

Two validated composite variables were used: the disease activity score (DAS 28) and the ACR20 responder rate. The DAS 28 was computed from the joint scores, the ESR and the patient's global assessment of disease activity. An ACR responder was defined as a patient with improvement of at least 20% of the baseline values in the tender joint count, swollen joint count and at least 3 of the following 5 variables: pain intensity, investigator global assessment, patient global assessment, HAQ disability index, or ESR.

Inclusion criteria were designed to enroll adult patients (18 to 80 years) with active RA who were typical of the general RA population being treated with a combination of stable corticoid medication and DMARDs. Patients had to have a documented history of RA and present with active symptoms of disease, i.e. morning stiffness of 45 min, pain ≥30 mm (VAS), ≥3 painful joints, ≥1 swollen joints and elevated ESR and/or CRP.

Patients had to have been treated with the following state-of-the-art RA medications for at least 3 months before entering the study:
DMARDs (unless they were not tolerated)
Prednis(ol)one, with a low, stable dose of 2.5 to 10 mg prednisone (or equivalent) for at least 1 month prior to screening.

Patients were to continue on their RA medications at the same dose throughout the 12-week double-blind treatment phase. These restrictions are considered appropriate because they ensure that any differences between the treatment groups were due to the different dosing modalities of prednisone not to dose changes in the corticoid or concomitant DMARDs.

Study Results 288 randomized patients were treated in total, 144 patients with Prednisone delayed-release and 144 with the IR reference product. The baseline characteristics of the two treatment groups were comparable (mean values for the overall population): age (55 years), gender (85% female), morning stiffness (173 min), disease duration (115 months), DAS 28 (5.9), daily dose of prednis(ol)one (6.6 mg), medications prior to screening (DMARDs 94%, non-steroidal anti-inflammatory drugs [NSAIDs] 80% patients). Also the medical history of the patients in both treatments are comparable. Table 1 summarizes the Disease characteristics. Patients with different disease duration (short, mid-term and long-lasting) and different disease activity (DAS: mild, moderate and severe) were included.

TABLE 1

Disease characteristics at baseline (ITT population)

| Disease characteristics at baseline | | Prednisone delayed-release (N = 144) | Standard IR prednisone (N = 144) | Total (N = 288) |
|---|---|---|---|---|
| RA | | | | |
| No. of Subjects | n(%) | 144 (100.0) | 144 (100.0) | 288 (100.0) |
| Mean Duration | months | 115.1 | 115.4 | 115.3 |
| Duration | <2 years, n (%) | 19 (13.2) | 18 (12.5) | 37 (12.8) |
| | 2-5 years, n (%) | 37 (25.7) | 37 (25.7) | 74 (25.7) |
| | 5-10 years, n(%) | 33 (22.9) | 31 (21.5) | 64 (22.2) |
| | >10 years, n (%) | 55 (38.2) | 58 (40.3) | 113 (39.2) |
| Pre-treatment | (yes) | 144 (100.0) | 144 (100.0) | 288 (100.0) |
| Stable dose [mg] of prednis(ol)one | Mean | 6.5 | 6.7 | 6.6 |
| DAS28 | | | | |
| | Mean | 5.8 | 5.9 | 5.9 |
| | SD | 0.8 | 0.9 | 0.8 |
| | Range | 3.3-8.1 | 3.7-7.7 | 3.3-8.1 |
| Disease activity (physician's Assessment) [n(%)] | Asymptomatic | 0 (0.0) | 0 (0.0) | 0 (0.0) |
| | Mild | 13 (9.0) | 14 (9.7) | 27 (9.4) |
| | Moderate | 103 (71.5) | 102 (70.8) | 205 (71.2) |
| | Severe | 28 (19.4) | 28 (19.4) | 56 (19.4) |
| | Very Severe | 0 (0.0) | 0 (0.0) | 0 (0.0) |
| Pain Intensity (HAS-VAQ) [mm] | mean | 57.9 | 59.7 | 58.8 |
| | SD | 14.8 | 15.8 | 15.3 |
| | Range | 18-95 | 25-96 | 18-96 |
| HAS-DI score | mean | 1.5 | 1.5 | 1.5 |
| | SD | 0.6 | 0.5 | 0.5 |
| | Range | 0.0-2.9 | 0.0-2.8 | 0.0-2.9 |

Efficacy Results

Primary efficacy variable and morning stiffness. As planned, the primary efficacy analysis in the study was performed on the intention-to-treat population (i.e. all randomized patients as randomized) using "last observation carried forward" methodology.

TABLE 2

Duration of morning stiffness after 12 weeks of treatment (intention-to-treat population)

| Duration of morning stiffness (mean (SD)) | Prednisone delayed-release (N = 144) | Prednisone Standard (N = 144) |
| --- | --- | --- |
| Baseline [min] | 164.1 (101.4) (N = 125) | 182.5 (125.0) (N = 129) |

At the end of the first week of treatment there was a difference of 10% between the two treatment groups. The relative reduction between baseline and final week of treatment was 22.7% in the Prednisone delayed-release group and 0.4% in the standard prednisone group. Thus, Prednisone delayed-release was shown to be superior to standard prednisone IR tablet in a statistically significant manner ($p<0.025$, one sided) and the primary study objective was met.

A difference between the two groups is obvious from the first week on, however the longer the treatment the more pronounced are the differences in favour for Prednisone delayed-release. This is illustrated in Table 3 and FIG. 1:

TABLE 3

Mean daily duration of morning stiffness per week (intention-to-treat population)

| Mean daily duration of morning stiffness per week (mean (SD)) | Prednisone delayed-release (N = 144) | Prednisone Standard (N = 144) |
| --- | --- | --- |
| Baseline [min] | 164.1 (101.4) (N = 125) | 182.5 (125.0) (N = 129) |
| At Week 1 [min] | 159.4 (127.3) (N = 126) | 186.4 (135.6) (N = 131) |
| Relative change [%] | −1.4 (62.4) (N = 124) | 9.3 (60.2) (N = 129) |
| At Week 2 [min] | 144.9 (136.4) (N = 123) | 187.7 (154.4) (N = 131) |
| Relative change [%] | −12.5 (70.0) (N = 121) | 8.1 (71.6) (N = 129) |
| At Week 3 [min] | 138.3 (137.1) (N = 122) | 164.2 (137.2) (N = 127) |
| Relative change [%] | −13.8 (73.9) (N = 120) | 0.3 (63.6) (N = 125) |
| At Week 4 [min] | 129.5 (128.3) (N = 117) | 163.7 (124.2) (N = 123) |
| Relative change [%] | −23.3 (54.7) (N = 115) | 3.5 (72.5) (N = 121) |
| At Week 5 [min] | 126.0 (126.9) (N = 117) | 159.7 (128.5) (N = 121) |
| Relative change [%] | −25.9 (55.1) (N = 115) | 6.0 (85.1) (N = 119) |
| At Week 6 [min] | 117.9 (128.2) (N = 112) | 154.2 (123.7) (N = 119) |
| Relative change [%] | −28.3 (59.8) (N = 110) | 5.3 (82.5) (N = 117) |
| At Week 7 [min] | 109.0 (113.9) (N = 109) | 156.5 (144.9) (N = 119) |
| Relative change [%] | −33.5 (49.1) (N = 107) | −2.6 (74.2) (N = 117) |
| At Week 8 [min] | 98.7 (93.8) (N = 105) | 152.1 (125.3) (N = 116) |
| Relative change [%] | −37.1 (45.8) (N = 103) | −5.2 (62.5) (N = 114) |
| At Week 9 [min] | 90.7 (87.5) (N = 107) | 146.4 (123.1) (N = 116) |
| Relative change [%] | −41.3 (46.5) (N = 105) | −5.6 (68.8) (N = 115) |
| At Week 10 [min] | 92.7 (90.8) (N = 105) | 147.9 (134.1) (N = 117) |
| Relative change [%] | −40.5 (46.9) (N = 103) | −5.0 (83.0) (N = 116) |
| At Week 11 [min] | 95.9 (97.2) (N = 103) | 148.9 (136.4) (N = 116) |
| Relative change [%] | −37.7 (50.1) (N = 101) | −1.2 (95.8) (N = 115) |
| At Week 12 [min] | 98.1 (100.5) (N = 102) | 149.5 (134.8) (N = 111) |
| Relative change [%] | −33.1 (75.4) (N = 100) | −3.4 (92.1) (N = 111) |

TABLE 2-continued

Duration of morning stiffness after 12 weeks of treatment (intention-to-treat population)

| Duration of morning stiffness (mean (SD)) | Prednisone delayed-release (N = 144) | Prednisone Standard (N = 144) |
| --- | --- | --- |
| At Week 12 (Final week) [min] | 120.9 (140.5) (N = 127) | 157.4 (145.6) (N = 131) |
| Relative change [%] | −22.66 (89.1) (N = 125) | −0.39 (89.0) (N = 129) |
| Treatment difference | | |
| LS mean (SD) [%] | 22.4 (11.1) | |
| Lower limit of 95% CI | 0.493 | |
| p-value | 0.0226 (one-sided) | |

The primary variable was "the relative change in duration of morning stiffness from baseline at individual study end in the double-blind treatment phase", whereby the duration of morning stiffness was the difference between the time of resolution of morning stiffness and the time of awakening. The reduction in duration of morning stiffness under Prednisone delayed-release treatment was higher than under standard IR prednisone throughout the 12-week treatment period.

The weekly assessment of the mean daily duration of morning stiffness revealed that the decrease and thus the improvement begins already after 2 weeks of treatment in the Prednisone delayed-release group. The mean daily duration of morning stiffness continues to decrease steadily thereafter, whereas in the prednisone standard group, there was no clear tendency for the changes during the 12-week treatment.

This result is surprising as Karatay showed in 2002 that such an effects could not be expected.

Due to the superiority of Prednisone delayed-release against standard Prednisone of a reduction in the daily dose of e.g. 25-30% could be possible under In the Phase III trial the superiority of a very low dose of Prednisone in the new delayed-release tablet compared to standard IR prednisone could be shown supporting the proposed dose reduction.

Table 4 shows the frequencies of starting stable doses of prednisone in the Prednisone delayed-release and standard prednisone groups of the intention-to-treat (ITT) population. The frequency profiles in both treatment groups were similar, with the most common dose being 5 mg (50% subjects), followed by 7 and 10 mg (approximately 20% each).

TABLE 4

Frequencies of stable doses of prednisone at start of study (ITT population)

| Stable Prednisone Dose (mg) | Number (%) subjects | |
|---|---|---|
| | Prednisone delayed-release (N = 144) | Standard prednisone (N = 144) |
| 2 | 1 (0.7) | 0 (—) |
| 3 | 8 (5.6) | 2 (1.4) |
| 4 | 1 (0.7) | 1 (0.7) |
| 5 | 72 (50.0) | 73 (50.7) |
| 6 | 1 (0.7) | 0 (—) |
| 7 | 28 (19.4) | 30 (20.8) |
| 8 | 4 (2.8) | 3 (2.1) |
| 9 | 0 (—) | 0 (—) |
| 10 | 29 (20.1) | 35 (24.3) |

The median value of the mean daily prednisone dose across all subjects in the ITT population was 5.18 mg.

Subgroup analyses were performed on the primary efficacy variable (i.e. the relative change from baseline in duration of morning stiffness) in subjects with a mean daily prednisone dose ≤5.18 mg and >5.18 mg.

In order to investigate the comparability of subgroups, selected demographic and baseline characteristics were analyzed: age, gender, ethnic origin, body weight, body height, duration of RA, HAQ-DI, pain intensity (VAS), SF36, and DAS28. Comments on age, duration of RA, and DAS28 as the most clinically relevant parameters are included below. There were no clinically relevant imbalances between subgroups in the other baseline variables.

Descriptive statistics for baseline demographics and the primary efficacy variable are presented for mean daily prednisone doses of >5.18 mg and ≤5.18 mg in each of the treatment groups of the ITT population in Table 5. The difference for the primary efficacy variable between the treatment groups is also given (as calculated by ANOVA, model A).

TABLE 5

Baseline demographic variables and primary efficacy variable in subjects with a mean daily prednisone dose <5.18 mg or >5.18 mg* (ITT population)

| Variable/subgroup | Prednisone delayed-release (N = 144) | | Standard prednisone (N = 144) | |
|---|---|---|---|---|
| | N | Mean (SD) | N | Mean (SD) |
| Baseline demographic variables | | | | |
| Age, years | | | | |
| Mean daily dose ≤5.18 mg* | 78 | 55.1 (10.5) | 65 | 54.6 (11.9) |
| Mean daily dose >5.18 mg* | 65 | 54.3 (12.0) | 77 | 56.1 (10.9) |
| Duration of RA, months | | | | |
| Mean daily dose ≤5.18 mg* | 77 | 115.5 (98.4) | 65 | 113.0 (111.4) |
| Mean daily dose >5.18 mg* | 65 | 116.3 (86.8) | 77 | 117.1 (75.1) |
| DAS28 score | | | | |
| Mean daily dose ≤5.18 mg* | 78 | 5.8 (0.8) | 64 | 5.8 (0.9) |
| Mean daily dose >5.18 mg* | 65 | 5.8 (0.7) | 76 | 6.0 (0.8) |
| Duration of morning stiffness | | | | |
| Mean daily dose ≤5.18 mg* | | | | |
| Baseline, min | 67 | 163.54 (109.92) | 59 | 174.79 (132.47) |
| Final week, min | 69 | 119.25 (132.40) | 60 | 169.36 (174.47) |
| Relative change from baseline to final week, % | 67 | −26.93 (67.72) | 59 | 7.88 (106.38) |
| Difference between groups | | | | |
| LS mean (SE), % | | 34.98 (15.57) | | |
| 95% CI | | 4.13, 65.83 | | |
| p-value | | 0.0134 (one-sided) | | |
| Mean daily dose >5.18 mg* | | | | |
| Baseline, min | 57 | 164.81 (92.36) | 68 | 189.74 (120.43) |
| Final week, min | 57 | 122.81 (152.12) | 69 | 144.22 (113.49) |
| Relative change from baseline to final week, % | 57 | −17.64 (110.12) | 68 | −8.76 (70.83) |
| Difference between groups | | | | |
| LS mean (SE), % | | 15.45 (16.14) | | |
| 95% CI | | −16.54, 47.45 | | |
| p-value | | 0.1702 (one-sided) | | |

*5.18 mg is the median value of the mean daily prednisone dose across all subjects in the ITT population.
LS = least square,
SE = standard error There were no differences in mean age, mean duration of RA, or mean DAS28 score between subjects receiving a mean daily prednisone dose of ≤5.18 mg and those receiving a mean daily dose of >5.18 mg in either of the 2 treatment groups.

In the Prednisone delayed-release group, morning stiffness decreased in both dose subgroups, with a larger decrease in subjects with a mean daily prednisone dose ≤5.18 mg than in subjects with a daily dose >5.18 mg.

In the standard prednisone group, subjects with a mean daily dose ≤5.18 mg showed an increase in the duration of morning stiffness. In subjects with a mean daily dose >5.18 mg, morning stiffness decreased but the decrease was not as large as in either of the Prednisone delayed-release dose subgroups.

Recurrence of Stiffness During the Day

In about 58% of the subjects in both treatment groups, recurrence of stiffness during the day was reported at baseline. After two weeks of treatment, the percentage was slightly lower in both treatment groups; after six weeks of treatment, the percentages were notably lower in both treatment groups with no major difference between the treatments; after 12 weeks of treatment, the percentage of subjects concerned was again notably lower compared to the 6-week value in both treatment groups.

Secondary Efficacy Variables.

TABLE 6

Intensity of pain (VAS) after 12 weeks of treatment (intention-to-treat population)

| Intensity of pain (VAS) (mean (SD)) | Prednisone delayed-release (N = 144) | Prednisone Standard (N = 144) |
| --- | --- | --- |
| Baseline [mm] | 50.9 (15.2) (N = 141) | 52.3 (17.2) (N = 143) |
| At Week 12 (Final week) [mm] | 45.7 (24.1) (N = 142) | 45.1 (23.1) (N = 144) |
| Relative change [%] | −8.57 (55.0) (N = 141) | −6.53 (83.9) (N = 143) |

According to the relative changes, the intensity of pain (VAS) was improved after 12 weeks of treatment by both treatments. In the ITT set, the treatment difference in the relative change in intensity of pain (VAS) was calculated to be 4.91% (SD 8.08%). A difference between the 2 groups in favour of Prednisone delayed-release has been observed, which was much more pronounced in the per-protocol set (−19% for Prednisone delayed-release vs-5% for Prednisone standard). The mean number of days with analgesics per week did not change notably after treatment start in both treatment groups. There is no difference between the two treatment groups after 2, 6, and 12 weeks of treatment. However, as under Prednisone delayed-release the intensity of pain went down it can be assumed that in patients with early RA or under long-term treatment also a reduction of painkillers will be seen.

No differences were observed in all other efficacy variables as listed in the following.

Quality of Sleep

The mean daily quality of sleep (VAS) did not improve in both treatment groups. There were no marked differences between baseline of the two treatment groups and the means of absolute changes after 2, 6, and 12 weeks of treatment.

Disease Activity Score (DAS 28)

The Disease Activity Score (DAS 28) decreased in both treatment groups. After two weeks of treatment, the decreases were small, whereas after six and 12 weeks of treatment the decreases were more pronounced. Absolute and relative changes were similar between the two treatment groups after 2, 6, and 12 weeks of treatment.

Tender and Swollen Joint Count

The tender and swollen joint count decreased in both treatment groups. After two weeks of treatment, the decreases were notable and further decreases were observed in both treatment groups after six and 12 weeks of treatment.

Subject's Global Assessment of Disease Activity

The mean subject's global assessment of disease activity (VAS) decreased in both treatment groups after start of the treatment with no relevant differences between timepoints and treatments.

Health Assessment Questionnaire Disability Index (HAQ-DI) and Quality of Life (SF36)

The HAQ-D1 and SF36 scores were similar in both treatment groups at baseline as well as after 12 weeks of treatment.

Physician's Global Assessment of Disease Activity

In both treatment groups, the number and percentage of subjects whose disease activity was assessed by the physician as mild increased during the course of the treatment; the number and percentage of subjects whose disease activity was assessed by the physician as severe decreased.

Inflammatory Signs

The mean values of the inflammatory signs CRP and IL-6 at baseline as well as after 2, 6 and 12 weeks of treatment and the respective relative changes are presented in Table 7.

TABLE 7

Inflammatory signs (CRP, IL-6) (intention-to-treat population)

| Inflammatory signs (median (min, max)) | Prednisone delayed-release | Prednisone Standard |
| --- | --- | --- |
| CRP [mg/L] | | |
| Baseline (Visit 2) | 9.9 (1.0, 105.1) | 12.2 (1.0, 177.5) |
| At Week 2 (Visit 3) | 10.2 (1.0, 159.0) | 11.2 (1.0, 106.3) |
| Relative change [%] | 13.0 (−96.1, 543.2) | 0.0 (−93.1, 1535.4) |
| At Week 6 (Visit 4) | 9.9 (1.0, 90.3) | 10.7 (1.0, 152.5) |
| Relative change [%] | 8.0 (−93.4, 695.2) | 0.0 (−94.2, 2377.8) |
| At Week 12 (Visit 5*) | 9.1 (1.0, 185.0) | 11.5 (1.0, 145.3) |
| Relative change [%] | 2.4 (−98.2, 1419.6) | 0.0 (−93.0, 2605.6) |
| IL-6 [IU/L] | | |
| Baseline (Visit 1) | 860 (200, 23000) | 1110 (200, 20800) |
| At Week 12 (Visit 5*) | 470 (200, 9530) | 1080 (200, 22700) |
| Absolute change | −160 (−13460, 9080) | 0.0 (−16190, 18100) |
| Relative change [%] | −28.6 (−96.8, 2018) | 0.0 (−98.1, 3017) |

The median CRP values did not change notably during the 12-week treatment in both treatment groups.

IL-6 values decreased during the 12-week treatment in the Prednisone delayed-release treatment group, but remained unchanged in the prednisone standard treatment group. Median values seem to have been halved by the Prednisone delayed-release preparation and the overall range was much smaller after 12 weeks of treatment. The variability was very high in both groups. However, the change under Prednisone delayed-release from baseline to 12 weeks was significantly lower (p<0.001). Also, there was a statistically significant difference between the two treatment groups after 12 weeks.

Osteocalcin

Osteocalcin is a sensitive measure to the bone metabolism (Heshmati 1998). The mean osteocalcin values at baseline (screening) as well as after 12 weeks of treatment and the respective relative changes are presented in Table 8.

TABLE 8

Osteocalcin (intention-to-treat population)

| Osteocalcin [ng/mL] (mean (SD)) | Prednisone delayed-release | Prednisone Standard |
|---|---|---|
| Baseline (Visit 1) | 20.95 (11.31) | 20.04 (9.95) |
| At Week 12 (Visit 5*) | 20.40 (12.82) | 19.43 (9.49) |
| Relative change [%] | −1.7 (33.0) | 3.9 (46.4) |

There were no differences between baseline and endpoints or between the two treatments. Thus, it can be concluded that night-time administration of low dose prednisone does not have a negative impact on bone metabolism and risk of osteoporosis.

Continued Efficacy Over During 9 Month Open Follow Up

Out of 288 patients enrolled into the double blind treatment period, a total of 249 subjects entered the open follow-up phase of the study, 219 subjects completed this phase (see Table 9).

TABLE 9

Disposition of Subjects

| Criterion | Number of subjects n (%) |
|---|---|
| Enrolled into double-blind phase | 288 |
| Enrolled in open follow-up | 249 (100) |
| Withdrawn | 30 (12.0*) |
| Who completed open follow-up | 219 (88.0*) |

Although efficacy was not the main objective of this open follow-up study, the order of reporting was kept the same as in the previous study report on the double-blind phase. In the open follow-up phase the interpretation of the efficacy data was focused on the following three aspects:

- maintenance of the effects on stiffness duration achieved by prednisone delayed-release during the double-blind phase in the former prednisone delayed-release group
- reduction of morning stiffness to the same extent in the subjects of the former prednisone standard group after three months of treatment with prednisone delayed-release at Visit 6
- further reduction of morning stiffness in the study population after Visit 6 up to 9 months (Visit 8) or after 12 months of treatment with prednisone delayed-release, respectively.

Mean Daily Duration of Morning Stiffness

Figure 2:
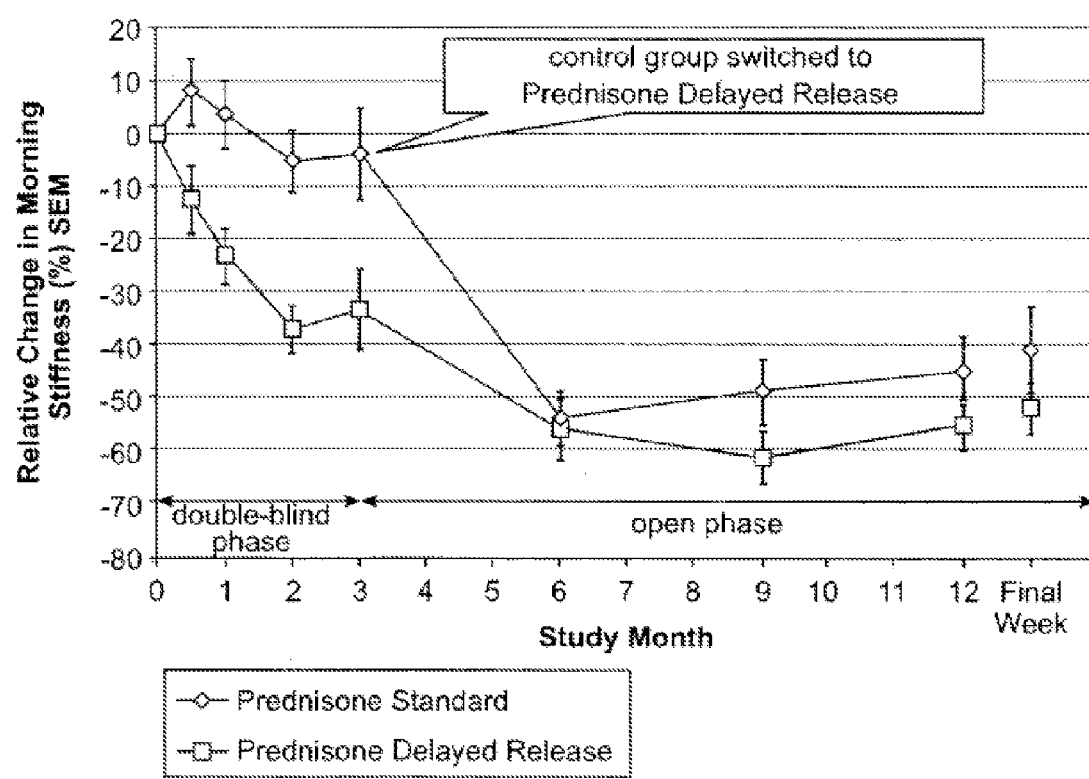
FIG. 2 shows duration of Morning Stiffness: Relative Change from Baseline in % (SEM) per month of treatment in the ITT population.

The mean daily duration of morning stiffness at start of the double-blind period (Visit 2), at start of the open follow-up period (Visit 5) and at end of study (Visit 8) as well as the relative changes are presented in Table 10 and FIG. 2 for the study population.

TABLE 10

Mean Daily Duration of Morning Stiffness at Month 9 of Follow-Up (Visit 8)

| Duration of morning stiffness [min] | Number of subjects mean (SD) median (min; max) | mean (SD) median (min; max.) | mean (SD) median (min; max) |
|---|---|---|---|
| Visit 2 (Start of Double-blind Period) | 156.27 (97.25) 137.14 (41.43; 659.29) (n = 107) | 182.40 (127.43) 149.29 (32.14; 720.0) (n = 115) | 169.80 (114.38) 143.21 (32.14; 720.0) (n = 222) |
| Visit 5 (Start of Follow-up Period) | 98.20 (100.22) 75.36 (0.0; 470.0) (n = 114) | 150.31 (139.48) 116.07 (0.0; 720.0) (n = 126) | 125.56 (124.92) 83.93 (0.0; 720.0) (n = 240) |
| Relative change [%] to Visit 2 | −34.47 (68.99) −37.29 (−100.00; 433.53) (n = 101) | −1.44 (93.07) −19.05 (−100.00; 609.86) (n = 112) | −17.10 (83.99) −28.75 (−100.00; 609.86) (n = 213) |
| Visit 8* (Month 9 of Follow-up) | 73.43 (92.32) 42.14 (0.0; 502.5) (n = 97) | 92.88 (124.59) 60.0 (0.0; 720.0) (n = 107) | 83.63 (110.60) 46.43 (0.0; 720.0) (n = 204) |
| Relative change [%] to Visit 2 | −55.07 (44.79) −63.13 (−100; 133.33) (n = 87) | −44.90 (63.73) −62.96 (−100; 269.44) (n = 97) | −49.71 (55.67) −63.02 (−100; 269.44) (n = 184) |
| Relative change [%] to Visit 5 | −7.81 (144.62) −38.33 (−100; 783.75) (n = 78) | −13.90 (146.98) −40.70 (−100; 950) (n = 99) | −11.22 (145.56) −40.70 (−100; 950) (n = 177) |

*Incl. premature termination

Starting treatment with prednisone delayed-release with longer stiffness duration at Visit 5, the former prednisone standard group achieved almost identical reduction, when percent relative change is calculated from Visit 8 to Visit 5 or from Visit 8 to Visit 2. For all subjects of the study population in the follow-up phase, a further mean reduction of 11.22% (Visit 8 compared to Visit 5) was gained. The total reduction of stiffness duration by 49.71% was observed on long term treatment between Visit 2 and 8.

Mean Daily Duration of Morning Stiffness after Start of Treatment with Prednisone Delayed-Release (Visit 2/Visit 5)

The mean daily duration of morning stiffness at start of the double-blind period (Visit 2) as well as at start of the follow-up period (Visit 5) and after 3, 6, 9, and 12 months (3-month intervals) of prednisone delayed-release treatment including respective relative changes are presented in Table 11.

TABLE 11

Mean Daily Duration of Morning Stiffness after Start of Treatment with Prednisone delayed-release (Visit 2/Visit 5)

| | Number of subjects | | |
|---|---|---|---|
| Mean daily duration of morning stiffness | Prednisone delayed-release (N = 249) mean (SD) | Prednisone Standard (N = 249) mean (SD) | Total (N = 249) mean (SD) |
| Visit 2 (Start of Double-blind Period) [min] | 156.27 (97.25) (n = 107) | — | 153.04 (121.71) (n = 233) |
| Visit 5 (Start of Follow-up Period) [min] | — | 150.31 (139.48) (n = 126) | |
| after 3 months of Prednisone delayed-release treatment [min] | 98.20 (100.22) (n = 114) | 85.17 (112.45) (n = 106) | 91.92 (106.25) (n = 220) |
| Relative change [%] | −34.47 (68.99) (n = 101) | −46.06 (46.86) (n = 98) | −40.18 (59.27) (n = 199) |
| after 6 months of Prednisone delayed-release treatment [min] | 65.70 (100.95) (n = 96) | 81.08 (104.79) (n = 115) | 74.08 (103.10) (n = 211) |
| Relative change [%] | −56.06 (54.20) (n = 86) | −32.83 (116.64) (n = 108) | −43.13 (94.71) (n = 194) |
| after 9 months of Prednisone delayed-release treatment* [min] | 62.43 (87.49) (n = 101) | 92.88 (124.59) (n = 107) | 78.10 (108.99) (208) |
| Relative change [%] | −61.35 (45.67) (n = 88) | −13.90 (146.98) (n = 99) | −36.23 (113.67) (n = 187 |
| after 12 months of Prednisone delayed-release treatment* [min] | 73.43 (92.32) (n = 97) | | |
| Relative change [%] | −55.07 (44.79) (n = 87) | | |

Relative changes refer to values given in bold case
*Incl. premature termination In Table 11 the duration of morning stiffness is presented as treatment duration of prednisone delayed-release independent from Visits. Relative changes were calculated from the data at Visit 2 for the former prednisone delayed-release group and from the data of Visit 5 for the former prednisone standard group. Taking advantage of the higher number of available data, the interpretation of the results was carried out for the total numbers.

Before starting with the treatment of prednisone delayed-release the mean daily duration of morning stiffness was 153 min. After three months of treatment stiffness duration was reduced to a mean of 92 min and after six months further to 74 min. After nine months of prednisone delayed-release treatment mean daily duration of morning stiffness was 78 min. For the subjects of the former prednisone delayed-release group data were also available after 12 months of prednisone delayed-release treatment. For these subjects stiffness duration was similar to those after six and nine months of treatment (73 min). No weaning of effects was observed. Thus, the mean duration of morning stiffness was reduced to the half after six months of prednisone delayed-release treatment.

Inflammatory Signs

Figure 3:
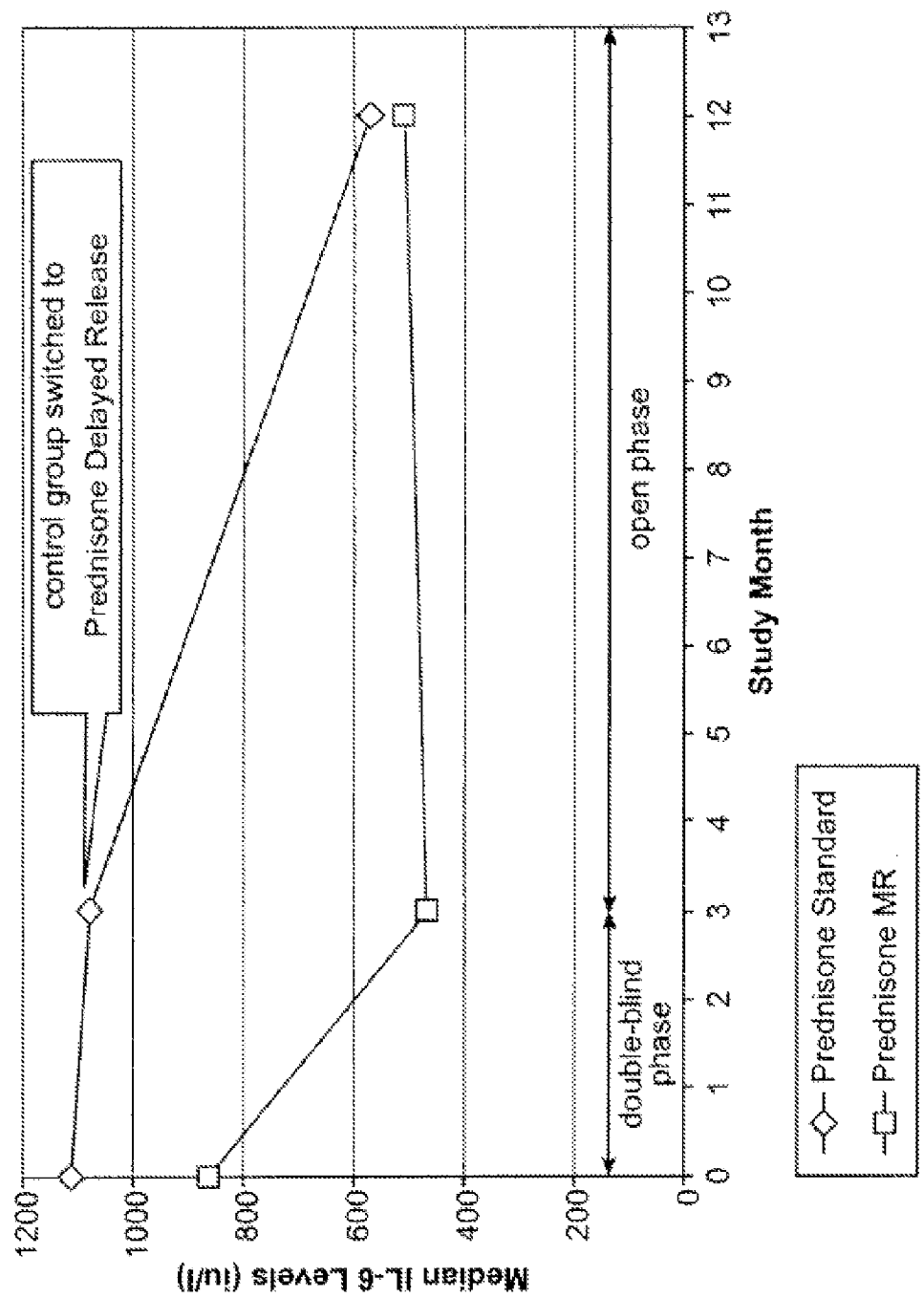
FIG. 3 shows IL 6 values (median) under treatment of Prednisone delayed release tablets.

The median values of the inflammatory signs CRP and IL-6 during the open follow-up period (Visit 5 to Visit 8) and the respective absolute changes are presented in Table 12 and FIG. 3.

TABLE 12

Inflammatory Signs (CRP, IL-6)

| | Number of subjects | | |
|---|---|---|---|
| Inflammatory signs | Prednisone delayed-release (N = 120) median (min; max) | Prednisone Standard (N = 129) median (min; max) | Total (N = 249) median (min; max) |
| CRP* [mg/L] | | | |
| Visit 5 (Start of Follow-up) | 8.60 (n = 120) (1.00; 139.80) | 10.90 (n = 129) (1.00; 145.30) | 9.40 (n = 249) (1.00; 145.30) |
| Visit 6 (Month 3 of Follow-up) | 8.55 (n = 108) (1.00; 81.40) | 8.15 (n = 118) (1.00; 152.40) | 8.35 (n = 226) (1.00; 152.40) |
| Absolute change | −0.45 (n = 108) (−131.20; 77.70) | −1.20 (n = 118) (−123.20; 95.00) | −0.70 (n = 226) −131.20; 95.00) |
| Visit 7 (Month 6 of Follow-up) | 7.00 (n = 109) (1.00; 71.00) | 9.05 (n = 118) (1.00; 69.70) | 8.00 (n = 227) (1.00; 71.00) |
| Absolute change | −0.60 (n = 109) (−122.60; 49.00) | −0.95 (n = 118) (−108.10; 25.80) | −0.80 (n = 227) (−122.60; 49.00) |
| Visit 8*** (Month 9 of Follow-up) | 8.40 (n = 112) (1.00; 83.30) | 8.35 (n = 124) (1.00; 86.50) | 8.35 (n = 236) (1.00; 86.50) |
| Absolute change | −0.25 (n = 112) (−129.10; 68.30) | −0.25 (n = 124) (−76.90; 68.70) | −0.25 (n = 236) (−129.10; 68.70) |

TABLE 12-continued

Inflammatory Signs (CRP, IL-6)

| | Number of subjects | | |
|---|---|---|---|
| Inflammatory signs | Prednisone delayed-release (N = 120) median (min; max) | Prednisone Standard (N = 129) median (min; max) | Total (N = 249) median (min; max) |
| IL-6** [IU/L] | | | |
| Visit 5 (Start of Follow-up) | 460 (n = 120) (200; 9530) | 1050 (n = 127) (200; 22700) | −710 (n = 247) (200; 22700) |
| Visit 8*** (Month 9 of Follow-up) | 510 (n = 111) (200; 18300) | 570 (n = 123) (200; 8100) | −525 (n = 234) (200; 18300) |
| Absolute change | 0 (n = 111) (−6830; 16110) | −300 (n = 121) (−20600; 6270) | −45 (n = 232) (−20600; 16110) |

*Values <1.0 mg/L were set to 1.0 for analysis
**Values <200 IU/L were set to 200 for analysis
***Incl. premature termination.

The median CRP values did not change notably during the nine months of open follow-up treatment with prednisone delayed-release, except in the former prednisone standard group at Visit 6 where the CRP value was decreased most compared to Visit 5.

As the variability of the IL-6 values was high in both groups, the median was chosen for comparison rather than the mean values. IL-6 values decreased notably in the former prednisone standard group from 1050 IU/L to 570 IU/L. Thus, IL-6 concentrations were halved in the subjects of the former standard group. This decrease of IL-6 was similar to the decrease of IL-6 in the prednisone delayed-release group described in the double-blind phase. No further reduction was observed in the subjects of the former prednisone delayed-release group.

Overview of Safety

The safety profile of glucocorticoids in the treatment of rheumatoid arthritis (RA) is well established). The main side effects consist of osteoporosis leading to fractures, gastrointestinal disorders, cardiovascular disorders, increased risk of infections, hyperglycemia, suppression of the HPA axis, and opthalmologic disorders. It is accepted that many of these side effects are observed at high or medium doses but not at low doses (Bijlsma et al. 2003, Bijlsma et al. 2005, Boers 2004, Buttgereit et al 2005, Conn 2001, Da Silva et al. 2005, Saag et al. 1994).

Prednisone delayed-release is intended for the treatment of RA at low doses (3 to 10 mg prednisone/day) and contains the same active drug ingredient as standard low-dose IR products. Prednisone delayed-release differs from standard products solely with respect to the recommended time of administration and timepoint of drug release within the gastrointestinal tract. The safety profile of low-dose prednisone is well established and reflected in labeling for standard IR products. Clinically significant differences are not expected.

Brief Summary of Adverse Events in Phase III Trial Under Prednisone Delayed-Release In this study, 59 (41.0%) subjects of the Prednisone delayed-release treatment group and 59 (41.0%) subjects of the prednisone standard treatment group experienced at least one treatment-emergent Adverse Event (AE). A total of 35 subjects (12.2%) experienced AEs that were considered by the investigator to be related to prednisone. AEs causing discontinuation of prednisone were experienced by 22 subjects (7.6%).

One subject receiving prednisone standard died on study within 18 days after first dose of prednisone. Seven subjects (2.4%) experienced SAEs, and in one subject of these 7 subjects, the SAE was judged to be related to prednisone by the investigator.

Table 13 summarizes the number of subjects experiencing AEs by type of AE (MedDRA Preferred Term, in at least 1.0% of the treated group).

TABLE 13

Most common AEs and drug-related AEs in study 003

| | No. (%) subjects with AE | | |
|---|---|---|---|
| Preferred Term | Prednisone delayed-release (N = 144) | Standard Prednisone (N = 144) | Total (N = 288) |
| All AEs | 59 (41.0) | 59 (41.0) | 118 (41.0) |
| Rheumatoid arthritis | 11 (7.6) | 13 (9.0) | 24 (8.3) |
| Abdominal pain | 5 (3.5) | 8 (5.6) | 13 (4.5) |
| Upper Nasopharyngitis | 4 (2.8) | 8 (5.6) | 12 (4.2) |
| Headache | 6 (4.2) | 4 (2.8) | 10 (3.5) |
| Flushing | 4 (2.8) | 6 (4.2) | 10 (3.5) |
| Nausea | 5 (3.5) | 4 (2.8) | 9 (3.1) |
| Drug-related AEs | 19 (13.2) | 16 (11.1) | 35 (12.2) |
| Abdominal pain | 3 (2.1) | 4 (2.8) | 7 (2.4) |
| Upper Nausea | 3 (2.1) | 3 (2.1) | 6 (2.1) |
| Headache | 4 (2.8) | 2 (1.4) | 6 (2.1) |
| Rheumatoid arthritis | 1 (0.7) | 4 (2.8) | 5 (1.7) |

The most frequently reported AEs (frequency >1.0% of the subjects of the safety set) by MedDRA Preferred Term were rheumatoid arthritis including several terms for worsening (deterioration, escalation, exacerbation, flare etc.) (24 subjects, 8.3%), abdominal pain upper (13 subjects, 4.5%) and nasopharyngitis (12 subjects, 4.2%). The incidences of these AEs were similar in treatment groups.

During the 9 month open follow-up period, 127 subjects (51.0%) experienced at least one treatment-emergent adverse event (AE). A total of 27 subjects (10.8%) experienced AEs that were by the investigator to be related to prednisone delayed-release. AEs causing discontinuation of prednisone delayed-release were experienced by 13 subjects (5.2%); 68 subjects (27.3%) had AEs not known to be recovered at the end of the study.

Table 14 summarizes the most common AEs by type of AE (MedDRA Preferred Term, in more than 2% of the subjects).

TABLE 14

Most Common Adverse Events (Frequency >1.0% Overall)

| Adverse Event (preferred term) | Total (N = 249) n (%) |
|---|---|
| Rheumatoid arthritis | 36 (14.5) |
| Flushing | 13 (5.2) |
| Upper respiratory tract infection | 7 (2.8) |
| Weight increased | 7 (2.8) |
| Back pain | 7 (2.8) |
| Bronchitis | 6 (2.4) |
| Hypercholesterolemia | 6 (2.4) |
| Arthralgia | 6 (2.4) |
| Nasopharyngitis | 6 (2.4) |
| Feeling hot | 5 (2.0) |

The most frequently reported AEs (MedDRA Preferred Term) were rheumatoid arthritis (36 subjects, 14.5%) and flushing (13 subjects, 5.2%). Flushing was only reported by the subjects who participated in the CRH testing. Upper respiratory tract infection, increased weight, or back pain were reported less frequently (seven subjects (2.8%) in each case).

Benefits and Risks Conclusions

Prednisone delayed-release is a novel, delayed-release tablet that has been developed to optimize the efficacy of orally administered low-dose prednisone in the treatment of RA. Prednisone delayed-release has shown improved efficacy compared to standard prednisone in patients with RA without increasing their prednisone dose. This improvement has been solely obtained as a result of Prednisone delayed-release's unique release characteristics. The safety profiles of Prednisone delayed-release and standard prednisone were comparable and the patients were thus not exposed to an increased risk.

The benefits and main features of Prednisone delayed-release can be summarized as follows:

A significant reduction of morning stiffness was obtained in patients with long-standing RA who were pretreated with prednisone and DMARDs. A decrease of 10% compared to baseline was already apparent at week 2 of treatment. Under continued treatment this reduction increased in magnitude and plateaued at about 30% to 40% from week 7 onwards. In 50% of the patients (median values), the duration of morning stiffness was reduced by at least one third (33.9%) during the double blind treatment phase. At the end of the 9 month open label follow-up period, a decrease in the duration of morning stiffness of 49% compared to baseline was observed (mean baseline duration of morning stiffness was 3 hours). Morning stiffness is one of the most distressing symptoms for RA patients and thus the observed sustained reduction for at least 12 months under Prednisone delayed-release can be considered a clinically meaningful improvement.

Both in the double blind and the 9 month open follow-up period, the reduction in morning stiffness was accompanied by a sustained parallel decrease in the pro-inflammatory cytokine IL-6, thus confirming the proposed pharmacological rationale for adapting the timing of prednisone administration to the circadian rhythm of RA.

These results are surprising because it could not be expected from former investigations (Karatay 2002). Also the long lasting effect of prednisone delayed-release over 12 months on reducing IL-6 levels is unexpected. Further, the long term correlation of IL-6 reduction and morning stiffness reduction could not be expected from former investigations.

Maximum plasma levels of prednisone in the early morning hours are obtained by administration of Prednisone delayed-release at about 22:00 which is an acceptable time for the patient.

Prednisone delayed-release tablets can be used in patients with severe, moderate or mild disease.

Prednisone delayed-release tablets can be used in patients with short, mid-term or long-lasting disease duration.

Prednisone delayed-release tablets can be used in patients pre-treated with corticosteroids, in those who are refractory to treatment or in corticoid naive patients.

Prednisone delayed-release tablets can be used as monotherapy or more likely in combination with DMARDs, NSAIDs, TNF a Inhibitors and/or analgetics.

Prednisone delayed-release tablets can be used for short, mid or long-term treatment.

LITERATURE REFERENCES

ACR (American College of Rheumatology) Subcommittee on Rheumatoid Arthritis Guidelines. Guidelines for the management of rheumatoid arthritis. Arthritis Rheum 2002; 46:328-46.

Ahlmen M, Nordenskiold U, Archenholtz B, Thyberg I, Ronnqvist R, Linden L, et al. Rheumatology outcomes: the patient's perspective. A multicentre focus group interview study of Swedish rheumatoid arthritis patients. Rheumatology 2005; 44:105-10.

Arnett F C, Edworthy S M, Bloch D A, McShane D J, Fries J F, Cooper N S, et al. The American Rheumatism Association 1987 revised criteria for the classification of rheumatoid arthritis. Arthritis Rheum 1988; 31:315-24.

Arvidson N G, Gudbjornsson B, Elf man L, Ryden A C, Totterman T H, Hallgren R. Circadian rhythm of serum interleukin-6 in rheumatoid arthritis. Ann Rheum Dis 1994; 53:521-4.

Arvidson N G, Gudbjornsson B, Larsson A, Hallgren R. The timing of glucocorticoid administration in rheumatoid arthritis. Ann Rheum Dis 1997; 56:27-31.

Bijlsma J W J, Boers M, Saag K G, Furst D E. Glucocorticoids in the treatment of early and late RA. Ann Rheum Dis 2003; 62:1033-7.

Bijlsma J W J, Saag, K G, Buttgereit F, da Silva J A P. Developments in glucocorticoid therapy. Rheum Dis Clin N Am 2005; 31:1-17.

Boers M. Glucocorticoids in rheumatoid arthritis: a senescent research agenda on the brink of rejuvenation? Best Practice Research Clin Rheumatol 2004; 18 (1):21-9.

Buttgereit F, Burmester G-R, Lipworth B J. Optimised glucocorticoid therapy: the sharpening of an old spear. Lancet 2005; 365:801-3.

Buttgereit F, Saag K G, Cutolo M, da Silva J A P, Bijlsma J W J. The molecular basis for the effectiveness, toxicity, and resistance to glucocorticoids: focus on the treatment of rheumatoid arthritis. Scand J Rheumatol 2005; 34:14-21.

Buttgereit F, Straub R H, Wehling M, Burmester G R. Glucocorticoids in the treatment of rheumatic diseases: an update on the mechanisms of action. Arthritis Rheum 2004; 50:3408-17.

Capell H A, Madhok R, Hunter J A, Porter D, Morrison E, Larkin J, et al. Lack of radiological and clinical benefit over two years of low dose prednisolone for rheumatoid arthritis: results of a randomised controlled trial. Ann Rheum Dis 2004; 63:797-803.

Carr A, Hewlett S, Hughes R, Mitchell H, Ryan S, Carr M, et al. Rheumatology outcomes: the patient's perspective.

J Rheumatol 2003; 30:880-3. [0214] Conn D L. Resolved: Low-dose prednisone is indicated as a standard treatment in patients with rheumatoid arthritis. Arthritis Rheum 2001; 45:462-7.

Crofford L J, Kalogeras K T, Mastorakos G, Magiakou M A, Wells J, Kanik K S, et al. Circadian relationships between interleukin (IL)-6 and hypothalamic-pituitary-adrenal axis hormones: failure of IL-6 to cause sustained hypercortisolism in patients with early untreated rheumatoid arthritis. J Clin Endocrinol Metab 1997; 82:1279-83.

Cutolo M, Maestroni G J M, Otsa K, Aakre O, Villaggio B, Capellino S, et al. Circadian melatonin and cortisol levels in rheumatoid arthritis patients in winter time: a north and south Europe comparison. Ann Rheum Dis 2005; 64:212-6.

Cutolo M, Masi A T. Circadian rhythms and arthritis. Rheum Dis Clin N Am 2005; 31:115-29.

Cutolo M, Seriolo B, Craviotto C, Pizzorni C, Sulli A. Circadian rhythms in RA. Ann Rheum Dis 2003; 62:593-6.

Da Silva J A P, Jacobs J W G, Kirwan J R, Boers M, Saag K G, Ines L B S, et al. Safety of low dose glucocorticoid treatment in rheumatoid arthritis: published evidence and prospective trial data. Ann Rheumatol Dis 2006; 65:285-93.

Gudbjornsson B, Skogseid B, Oberg K, Wide L, Hallgren R. Intact adrenocorticotropic hormone secretion but impaired cortisol response in patients with active rheumatoid arthritis. Effect of glucocorticoids. J Rheumatol 1996; 23:596-602.

Heshmati H M, Riggs B L, Burritt M F, McAlister C A, Wollan P C, Khosla S. Effects of the circadian variation in serum cortisol on markers of bone turnover and calcium homeostasis in normal postmenopausal women. J Clin Endocrinol Metab 1998; 83:751-6.

Hewlett S, Carr M, Ryan S, Kirwan J, Richards P, Carr A, et al. Outcomes generated by patients with rheumatoid arthritis: How important are they? Musculoskeletal Care 2005; 3:131-42.

Hickling P, Jacoby R K, Kirwan J R. Joint destruction after glucocorticoids are withdrawn in early rheumatoid arthritis. Arthritis and Rheumatism Council Low Dose Glucocorticoid Study Group. Br J Rheumatol 1998; 37:930-6.

Hudson M, Baron M. Morning stiffness is a better predictor of function in early inflammatory arthritis than are swollen and tender joints. Arthritis Rheum 2005; 52 Suppl 9: abstract 1036.

Jacobs J W G, van Everdingen A A, Verstappen S M M, Bijlsma J W J. Followup radiographic data on patients with rheumatoid arthritis who participated in a two-year trial of prednisone therapy or placebo. Arthritis Rheum 2006; 54:1422-8.

Karatay S. et al, The timing of low dose glucocorticoid therapy in the treatment of rheumatoid arthritis, The Pain Clinic, 2002, 13, 4, 305-312 Kirwan J R. The effect of glucocorticoids on joint destruction in rheumatoid arthritis. The Arthritis and Rheumatism Council Low-Dose Glucocorticoid Study Group. N Engl J Med 1995; 333: 142-6.

Kirwan J R, Boers M, Shea B. Glucocorticoids strongly suppress joint damage in rheumatoid arthritis: A meta-analysis of 1, 414 patients in 15 trials. Arthritis Rheum 2005; 52 Suppl 9: abstract 891.

LeLoet X et al, Clinical practice decision tree for the coice of the first disease modifying antirheumatic drug for very early rheumatoid arthritis: a 2004 proposal of the French Society of Rheumatology, Annals of Rheum Dis 2006; 65:45-50

Mastorakos G, Ilias I. Relationship between interleukin-6 (IL-6) and hypothalamic-pituitary-adrenal axis hormones in rheumatoid arthritis. Z Rheumatol 2000; 59(Suppl 2):75-9.

Petrovsky N, McNair P, Harrison L C. Diurnal rhythms of pro-inflammatory cytokines: regulation by plasma cortisol and therapeutic implications. Cytokine 1998; 10:307-12.

Pincus T, Sokka T, Kautiainen H. Patients seen for standard rheumatoid arthritis care have significantly better articular, radiographic, laboratory, and functional status in 2000 than in 1985. Arthritis Rheum 2005; 52:1009-19.

Saag K G, Criswell L A, Sems K M, Nettleman M D, Kolluri S. Low-dose corticosteroids in rheumatoid arthritis—A meta-analysis of their moderate-term effectiveness. Arthritis Rheum 1996; 39:1818-25.

Saag K G, Koehnke R, Caldwell J R, Brasington R, Burmeister L F, Zimmerman B, et al. Low dose long-term corticoid therapy in rheumatoid arthritis: an analysis of serious adverse events. Am J Med 1994; 96:115-23.

Stucki G, Cieza A. The international classification of functioning, disability and health (ICF) core sets for rheumatoid arthritis: a way to specify functioning. Ann Rheum Dis 2004; 63(Suppl 2):40-5.

Svensson B, Boonen A, Albertsson K, van der Heijde D, Keller C, Hafstrom J. Low-dose prednisolone in addition to the initial disease-modifying antirheumatic drug in patients with early active rheumatoid arthritis reduces joint destruction and increases the remission rate: a two-year randomized trial. Arthritis Rheum 2005; 52:3360-70.

van Everdingen A A, Jacobs J W G, Siewertsz van Reesema D R, Bijlsma J W J. Low-dose prednisone therapy for patients with early active rheumatoid arthritis: clinical efficacy, disease-modifying properties, and side effects. A randomized, double-blind, placebo-controlled clinical trial. Ann Intern Med 2002; 136:1-12.

van Staa T P, Leufkens H G M, Abenhaim L, Zhang B, Cooper C. Oral corticosteroids and fracture risk: relationship to daily and cumulative doses. Rheumatology 2000; 39:1383-9.

Wassenberg S, Rau R, Steinfeld P, Zeidler H. Very low-dose prednisolone in early rheumatoid arthritis retards radiographic progression over two years. Arthritis Rheum 2005; 52:3371-80.

I claim:

1. A method for the treatment of a patient suffering from signs and symptoms of an underlying rheumatic disease who had previously been treated with an oral immediate release dosage form of a glucocorticoid,
which method comprises administering daily, at or before bedtime, for at least about two weeks an effective amount of prednisone contained in a delayed-release dosage form to said patient who had previously been treated with an oral immediate release dosage form of a glucocorticoid,
wherein the delayed release dosage form is a tablet or a capsule.

2. The method of claim 1, wherein the treatment comprises administration of the prednisone contained in a delayed-release dosage form for at least about four weeks.

3. The method of claim 2, wherein the treatment comprises administration of the prednisone contained in a delayed-release dosage form for at least about eight weeks.

4. The method of claim 3, wherein the treatment comprises administration of the prednisone contained in a delayed-release dosage form one for at least about twelve weeks.

5. The method of claim 4, wherein the treatment comprises administration of the prednisone contained in a delayed-release dosage form for at least about twelve months.

6. The method of claim 1, wherein the rheumatic disease is rheumatoid arthritis, ankylosating spondylitis and/or polymyalgia rheumatica.

7. The method of claim 1, wherein the delayed-release dosage form has a lag time of from about 3 hours to about 5 hours after administration.

8. The method of claim 1, wherein the delayed-release dosage form has a dissolution time of equal to or less than about 2 hours after the lag time is reached.

9. The method of claim 1, wherein the delayed-release dosage form has a drug release behaviour which is independent of pH.

* * * * *